(12) United States Patent
Sekine et al.

(10) Patent No.: US 7,851,157 B1
(45) Date of Patent: Dec. 14, 2010

(54) OLIGONUCLEOTIDE DERIVATIVE, PROBE FOR DETECTION OF GENE, AND DNA CHIP

(75) Inventors: Mitsuo Sekine, Yokohama (JP); Kohji Seio, Yokohama (JP); Akihiro Ohkubo, Yokohama (JP); Kazushi Sakamoto, Yokohama (JP); Takeshi Sasami, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 485 days.

(21) Appl. No.: 11/892,673

(22) Filed: Aug. 24, 2007

(30) Foreign Application Priority Data

Feb. 28, 2005 (JP) .............................. 2005-053417

(51) Int. Cl.
*C12Q 1/68* (2006.01)
*C07G 3/00* (2006.01)
*C07H 21/02* (2006.01)
*C07H 21/00* (2006.01)
*C07H 21/04* (2006.01)

(52) U.S. Cl. ........................... 435/6; 536/4.1; 536/23.1; 536/24.3; 536/25.3

(58) Field of Classification Search .................. 536/4.1, 536/23.1, 24.3, 25.3; 435/6
See application file for complete search history.

(56) References Cited

FOREIGN PATENT DOCUMENTS

| EP | 1247815 A2 | 10/2002 |
|---|---|---|
| EP | 1247815 A3 | 10/2002 |
| JP | 09-507121 | 7/1997 |
| JP | 9-507248 | 7/1997 |
| JP | 2001-524926 | 12/2001 |
| JP | 2004-168684 | 6/2004 |
| JP | 2004-233217 | 8/2004 |
| JP | 2005-000162 | 1/2005 |
| JP | 2005-247771 A | 9/2005 |
| WO | WO-98/39348 | 9/1998 |
| WO | WO-99/21874 | 5/1999 |
| WO | WO-99/51775 A1 | 10/1999 |
| WO | WO-00/18778 | 4/2000 |

OTHER PUBLICATIONS

Fu, D.-J.et al., "Importance of Specific Adenosine $N^7$-Nitrogens for Efficient Cleavage by a Hammerhead Ribozyme. A Model for Magnesium Binding," Biochemistry, 1992, vol. 31, No. 45, pp. 10941 to 10949.
Mazzarelli, J.M. et al., "Interactions between the *trp* Repressor and Its Operator Sequence As Studied by Base Analogue Substitution," Biochemistry, 1992, vol. 31, pp. 5925 to 5936.
Seela, F. et al., "Pyrazolo [3,4-d] Pyrimidine 2'-Deoxyribo- and 2',3'-Dideoxyribo-Furanosides: Synthesis and Application to Oligonucleotide Chemistry," Nucleosides & Nucleotides, 1989, vol. 8, No. 5 & 6, pp. 789 to 792.
Seela, F. et al., "96. 2'-Deoxy-β-D-ribofuranosides of $N^6$-Methylated 7-Deazaadenine and 8-Aza-7-deazaadenine: Solid-Phase Synthesis of Oligodeoxyribonucleotides and Properties of Self-Complementary Duplexes," Helvetica Chimica Acta, 1989, vol. 72, pp. 868 to 881.
Heetebrij, R.J. et al., "A Versatile Approach Towards Regioselective Platinated DNA Sequences," Chem. Eur. J., 2003, vol. 9, No. 8, pp. 1823 to 1827.
Koizumi, M. et al., "Biologically Active Oligodeoxyribonucleotides. Part $12^1$: $N^2$-Methylation of 2'-Deoxyguanosines Enhances Stability of Parallel G-Quadruplex and Anti-HIV-1 Activity," Bioorganic & Medicinal Chemistry Letters, 2000, vol. 10, pp. 2213 to 2216.
Nielsen, J. et al., "Application of 2-cyanoethyl N,N,N',N'-tetraisopropylphosphorodiamidite for in situ preparation of deoxyribonucleoside phosphoramidites and their use in polymer-supported synthesis of oligodeoxyribonucleotides," Nucleic Acids Research, 1986, vol. 14, No. 18, pp. 7391 to 7403.
Gaytán, P. et al., "Orthogonal combinatorial mutagenesis: a codon-level combinatorial mutagenesis method useful for low multiplicity and amino acid-scanning protocols," Nucleic Acids Research, 2001, vol. 29, No. 3, e9.
Gaytan, P. et al., "Combination of DMT-mononucleotide and Fmoc-trinucleotide phosphoramidites in oligonucleotide synthesis affords an automatable codon-level mutagenesis method," Chemistry & Biology, 1998, vol. 5, pp. 519 to 527.
M. C. Pirrung, "How to Make a DNA Chip," Angew. Chem. Int. Ed. 2002, vol. 41, pp. 1276 to 1289.
X. Gao et al., "In Situ Synthesis of Oligonucleotide Microarrays," Biololymers, vol. 73, 2004, pp. 579 to 596.
Wada, T. et al., "Synthesis and hybridization ability of Oligodeoxyribonucleotides Incorporating N-Acyldeoxycytidine Derivatives," Eur. J. Org. Chem., 2001, pp. 4583-4593.
Seela, F. et al., "Bending of Oligonucleotides Containing an Isosteric Nucleobase: 7-Deaza-2'-deoxyadenosine Replacing dA within $d(A)_6$ Tracts," Biochemistry, 28, 1989, pp. 6193-6198.
Supplementary European Search Report dated Aug. 24, 2010, issued in the European Patent Application No. 06714901.3.

*Primary Examiner* — Jezia Riley
(74) *Attorney, Agent, or Firm* — Edwards Angell Palmer & Dodge LLP

(57) ABSTRACT

To provide an oligonucleotide derivative that can be used without a problem of falling of a DNA probe from a support.

The oligonucleotide derivative of the present invention is represented by the following General Formula (1). The oligonucleotide derivative of the present invention can be used in a DNA chip, a microarray, and so on and further used in a method of detecting gene and a method of regulating gene expression, for example.

[Formula 1]

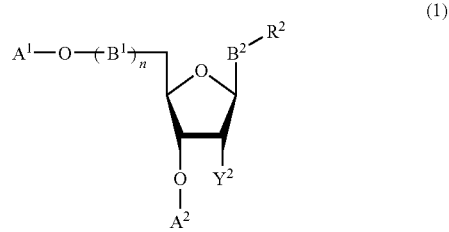

(1)

9 Claims, No Drawings

OLIGONUCLEOTIDE DERIVATIVE, PROBE FOR DETECTION OF GENE, AND DNA CHIP

TECHNICAL FIELD

The present invention relates to an oligonucleotide derivative, a probe for detection of gene, and so on. More specifically, the present invention relates to an oligonucleotide derivative, a probe for detection of gene, and so on which can be used without occurrence of problems such as falling of the probe.

BACKGROUND ART

Genetic analysis, including single nucleotide polymorphisms (SNPs) analysis, can provide a ground for so-called "tailor-made medicine", and the necessity thereof is increasing rapidly. From the viewpoint of reducing side effects of drugs, the U.S. Food and Drug Administration is shifted to require SNPs information in relation to the effect of a new drug when the new drug application is submitted. In also Japan, the necessity of SNPs analysis is increasing rapidly.

In DNA chips which are presently widely used in SNPs analysis, the detection probes are synthetic DNA oligonucleotides. The DNA chips are mainly prepared by one of the following two methods. The first method is to immobilize separately synthesized DNA oligonucleotides on a surface of a substrate such as a slide glass (coupling synthesis method, refer to Non-Patent Document 1). The second method is to synthesize oligonucleotides on a substrate such as a slide glass (in-situ synthesis method, refer to Non-Patent Document 2).

In the coupling synthesis method, first, a highly reactive functional group is attached to a DNA oligonucleotide to give a DNA probe. Then, the given DNA probe is spotted on a surface of a substrate such as a slide glass, and thereby the probe molecule is immobilized on the substrate by a covalent bond formed by a chemical reaction between the DNA probe and a functional group present in the substrate surface. In this method, since the method of spotting DNA probe is complicated, it is very difficult to control efficiency of immobilization to a substrate surface, which also influences on the quality control.

In in-situ synthesis method, a probe is synthesized on a surface of a substrate such as a slide glass by optical lithography or bubble jetting. In this method, since DNA is synthesized at a specific position, the immobilization reaction of a DNA probe on a substrate surface can be omitted. Therefore, high-throughput synthesis of DNA chips is possible. However, in this in-situ synthesis method, the elongation efficiency of a DNA strand on a substrate surface is low, and the DNA probe purity is low. Thus, there is a disadvantage of low correctness. For example, DNA elongation efficiency in synthesis by optical lithography is about 95% at highest. For example, valid probe ratio of a 20-base probe is not higher than 40%. In other words, sequences of 60% or more probes are incorrect.

Non-Patent Document 1: Ange wandte Chemie international edition, 2002, 41, 1276-1289

Non-Patent Document 2: Biopolymer, 2004, 73, 579-596

The presence of a large number of probes having incorrect sequences causes a lack of accuracy in results of analyses, such as SNP analysis, which are required to be accurate and is a problem.

In conventional processes of preparing probes, it is necessary to bind a protecting group to a nucleotide base and removing this protecting group by ammonia treatment, lastly. However, the ammonia treatment cleaves the Si—O bond at an anchor portion, and thereby about 90% of DNA probes are detached from a support.

Therefore, it is an object of the present invention to provide an oligonucleotide derivative which can be used without occurrence of the above-mentioned problems when used in SNP, for example.

It is another object of the present invention to provide a method of utilizing the oligonucleotide derivative for detection of gene.

MEANS FOR SOLVING THE PROBLEMS

In order to achieve the above mentioned objects, the present inventors have conducted intensive studies and, as a result, have found the fact that the above-mentioned objects can be achieved by using a specific oligonucleotide.

The present invention has been completed based on the above-mentioned finding and provides an oligonucleotide derivative represented by the following General Formula (1):

[Formula 1]

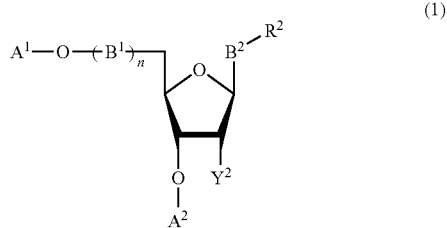

(1)

(where $A^1$ and $A^2$ may be the same or different and each represent a hydrogen atom, a hydroxyl group, an alkyl group, a phosphate group, or a trityl group which may be substituted by a substituent; n represents an integer of 10 to 50; $Y^2$ represents a hydrogen atom, a hydroxyl group, an alkoxy group, or a 2-cyanoethoxy group or may be bound to the carbon atom at the 4'-position of the ribose to form a ring; $B^2$ represents a natural or non-natural nucleotide base; $R^2$ represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); and $B^1$ represents a substituent represented by General Formula (2):

[Formula 2]

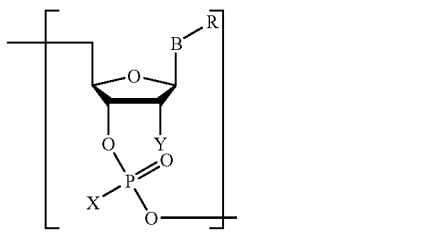

(2)

where B represents a natural or non-natural nucleotide base; R represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); X represents an oxygen ion, a sulfur ion, $BH_3$, $OCH_3$, or $CH_3$; and Y represents a hydrogen atom, a hydroxyl group, an alkoxy group, or a 2-cyanoethoxy group or may be bound to the carbon atom at the 4'-position of the ribose to form a ring, wherein at least one of R and $R^2$ is not a hydrogen atom).

Furthermore, the present invention provides a microarray for detection of gene. The microarray includes a support immobilized with at least an oligonucleotide derivative described above.

Furthermore, the present invention provides a DNA chip. The DNA chip includes a support immobilized with at least an oligonucleotide derivative described above.

Furthermore, the present invention provides a method of identifying a nucleotide in a target nucleic acid. The method includes the steps of hybridizing an oligonucleotide derivative represented by the following General Formula (1) to a target nucleic acid in a sample; and detecting the hybridization product:

[Formula 3]

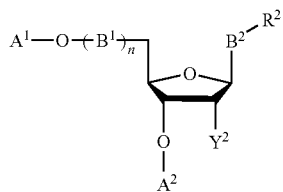

(1)

(where $A^1$ and $A^2$ may be the same or different and each represent a hydrogen atom, a hydroxyl group, an alkyl group, a phosphate group, or a trityl group which may be substituted by a substituent; n represents an integer of 10 to 50; $Y^2$ represents a hydrogen atom, a hydroxyl group, an alkoxy group, or a 2-cyanoethoxy group or may be bound to the carbon atom at the 4'-position of the ribose to form a ring; $B^2$ represents a natural or non-natural nucleotide base; $R^2$ represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); and $B^1$ represents a substituent represented by the following General Formula (2):

[Formula 4]

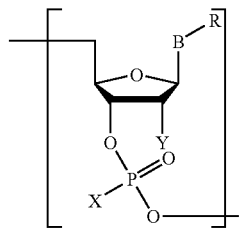

(2)

where B represents a natural or non-natural nucleotide base; R represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); X represents an oxygen ion, a sulfur ion, $BH_3$, $OCH_3$, or $CH_3$; and Y represents a hydrogen atom, a hydroxyl group, an alkoxy group, or a 2-cyanoethoxy group or may be bound to the carbon atom at the 4'-position of the ribose to form a ring, wherein at least one of R and $R^2$ is not a hydrogen atom).

Furthermore, the present invention provides a method of regulating gene expression by suppressing gene expression using an oligonucleotide derivative represented by the following General Formula (1):

[Formula 5]

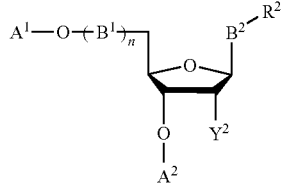

(1)

(where $A^1$ and $A^2$ may be the same or different and each represent a hydrogen atom, a hydroxyl group, an alkyl group, a phosphate group, or a trityl group which may be substituted by a substituent; n represents an integer of 10 to 50; $Y^2$ represents a hydrogen atom, a hydroxyl group, an alkoxy group, or a 2-cyanoethoxy group or may be bound to the carbon atom at the 4'-position of the ribose to form a ring; $B^2$ represents a natural or non-natural nucleotide base; $R^2$ represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); and $B^1$ represents a substituent represented by the following General Formula (2):

[Formula 6]

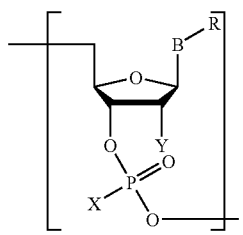
(2)

where B represents a natural or non-natural nucleotide base; R represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); X represents an oxygen ion, a sulfur ion, $BH_3$, $OCH_3$, or $CH_3$; and Y represents a hydrogen atom, a hydroxyl group, an alkoxy group, or a 2-cyanoethoxy group or may be bound to the carbon atom at the 4'-position of the ribose to form a ring, wherein at least one of R and $R^2$ is not a hydrogen atom).

Furthermore, the present invention provides a nucleotide derivative represented by General Formula (17):

[Formula 7]

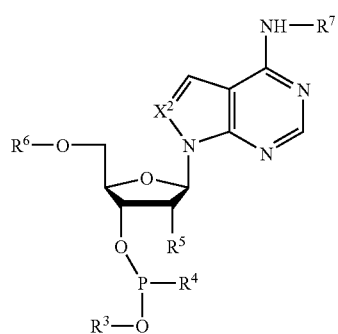
(17)

(where $R^3$ represents a phosphate-protecting group; $R^4$ represents a dialkylamino group having the same or different two alkyl groups each having one to six carbon atoms on its nitrogen atom; $R^5$ represents a hydrogen atom, an alkoxy group, or a trialkylsilyloxy group, a trialkylsilyloxymethoxy group, or a cyanoethyl group which has the same or different alkyl groups each having one to ten carbon atoms or is bound to the carbon atom at the 4'-position of the ribose to form a ring; $R^6$ represents a hydroxyl-protecting group; $R^7$ represents an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); and $X^2$ represents a nitrogen atom or a carbon atom which may have a substituent thereon).

Furthermore, the present invention provides a nucleotide derivative represented by General Formula (18):

[Formula 8]

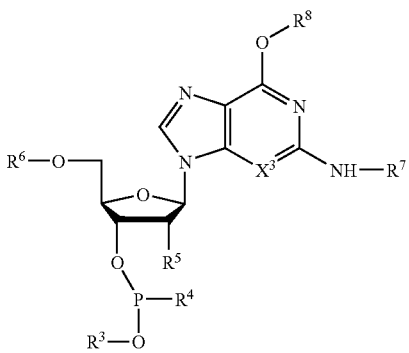
(18)

(where $R^3$ represents a phosphate-protecting group; $R^4$ represents a dialkylamino group having the same or different two alkyl groups each having one to six carbon atoms on its nitrogen atom; $R^5$ represents a hydrogen atom, an alkoxy group, or a trialkylsilyloxy group, a trialkylsilyloxymethoxy group, or a cyanoethyl group which has the same or different alkyl groups each having one to ten carbon atoms or is bound to the carbon atom at the 4'-position of the ribose to form a ring; $R^6$ represents a hydroxyl-protecting group; $R^7$ represents an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); $R^8$ represents a diphenylcarbamoyl group or a silyl group having the same or different three aryl or alkyl groups in total on its silicon atom; and $X^3$ represents a nitrogen atom or methine).

Furthermore, the present invention provides a nucleotide derivative represented by General Formula (19):

[Formula 9]

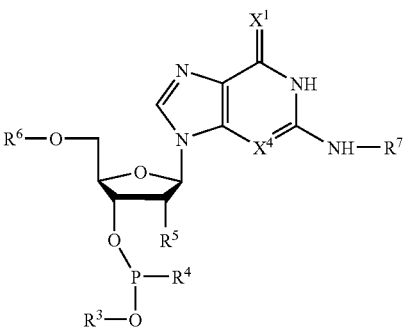
(19)

(where $R^3$ represents a phosphate-protecting group; $R^4$ represents a dialkylamino group having the same or different two alkyl groups each having one to six carbon atoms on its nitrogen atom; $R^5$ represents a hydrogen atom, an alkoxy group, or a trialkylsilyloxy group, a trialkylsilyloxymethoxy group, or a cyanoethyl group which has the same or different alkyl groups each having one to ten carbon atoms or is bound to the carbon atom at the 4'-position of the ribose to form a ring; $R^6$ represents a hydroxyl-protecting group; $R^7$ represents an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); $X^4$ represents a nitrogen atom or a methine group; and X' represents an oxygen atom or a sulfur atom).

ADVANTAGES OF THE INVENTION

The oligonucleotide derivative according to the present invention can discriminate a base even if it bears a protecting group.

The probes, the microarray, and the DNA chips according to the present invention utilize the oligonucleotide derivatives of the present invention, and thereby detection of gene can be performed with a high sensitivity.

The nucleotide derivative according to the present invention is used as a raw material for preparing the oligonucleotide derivative of the present invention.

BEST MODE FOR CARRYING OUT THE INVENTION

First, the oligonucleotide derivative according to the present invention will now be described.

The oligonucleotide derivative according to the present invention is represented by the following General Formula (1):

[Formula 10]

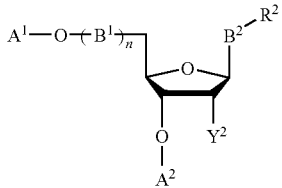

(1)

In General Formula (1), $A^1$ and $A^2$ may be the same or different and each represent a hydrogen atom, a hydroxyl group, an alkyl group, a phosphate group, or a trityl group which may be substituted by a substituent. The alkyl group preferably has 1 to 20 carbon atoms. In an alkyl group having more than 20 carbon atoms, the double strand-forming ability and the base-discriminating ability may be decreased. In addition, an alkyl group which is bound to the trityl group has 1 to 20 carbon atoms, for example.

Also, n represents an integer of 10 to 50. When n represents an integer less than 10, the double strand-forming ability is decreased. Contrarily, when n is higher than 50, the base-discriminating ability is decreased.

$Y^2$ represents a hydrogen atom, a hydroxyl group, an alkoxy group, or a 2-cyanoethoxy group ethyl group or may be bound to the carbon atom at the 4'-position of the ribose to form a ring. The alkoxy group preferably has 1 to 20 carbon atoms.

$B^2$ represents a natural or non-natural nucleotide base, and examples thereof include natural adenine, cytosine, guanine, thymine, and uracil; and artificial bases such as 7-deazaadenine, 7-deaza-8-azaadenine, 3-deazaadenine, 6-thioguanine, 2-thiouracil, 2-thiothymine, 7-deazaadenine substituted by a substituent (for example, an alkyl, alkenyl, alkynyl, halogen, nitro, acyl, or hydroxyl group) at the 7-position, adenine substituted by a substituent (for example, an alkyl, alkenyl, alkynyl, halogen, nitro, acyl, or hydroxyl group) at the 8-position, 7-deazaadenine substituted by a substituent (for example, an alkyl, halogen, nitro, acyl, or hydroxyl group) at the 8-position, 7-deazaadenine, 7-deazaguanine, 7-deaza-8-azaguanine, and 3-deazaguanine substituted by substituents (for example, an alkyl, alkenyl, alkynyl, halogen, nitro, acyl, or hydroxyl group) at the 7- and 8-positions, 7-deazaguanine substituted by a substituent (for example, an alkyl, alkenyl, alkynyl, halogen, nitro, acyl, or hydroxyl group) at the 7-position, guanine substituted by a substituent (an alkyl, alkenyl, alkynyl, halogen, nitro, acyl, or hydroxyl group) at the 8-position, 7-deazaguanine substituted by a substituent (for example, an alkyl, alkenyl, alkynyl, halogen, nitro, acyl, or hydroxyl group) at the 8-position, 7-deazaguanine substituted by substituents (for example, an alkyl, alkenyl, alkynyl, halogen, nitro, acyl, or hydroxyl group) at the 7- and 8-positions, cytosine substituted by a functional group (for example, an alkyl, alkenyl, alkynyl, halogen, nitro, acyl, or hydroxyl group) at the 5-position, pseudo-isocytosine, pseudo-isocytosine substituted by a functional group (for example, an alkyl, alkenyl, alkynyl, acyl, or hydroxyl group) at the 1-position, uracil substituted by a functional group (for example, an alkyl, alkenyl, alkynyl, halogen, nitro, acyl, or hydroxyl group) at the 5-position, pseudo-uracil, and pseudo-uracil substituted by a functional group (for example, an alkyl, alkenyl, alkynyl, acyl, or hydroxyl group) at the 1-position.

$R^2$ represents a substituent bound to an amino group of the nucleotide base. Therefore, when $B^2$ does not have an amino group, the nucleotide base does not have $R^2$. Examples of $R^2$ include hydrogen atoms, acyl groups, thioacyl groups, alkoxycarbonyl groups, alkoxythiocarbonyl groups, carbamoyl groups which may be substituted by alkyl groups, thiocarbamoyl groups which may be substituted by alkyl groups, and alkyl groups (which may be bound to alkyl groups, alkenyl groups, alkynyl groups, or phenyl groups). The alkyl groups preferably have 1 to 30 carbon atoms. In addition, the alkyl groups, the alkenyl groups, and the alkynyl groups which are bound to the alkyl groups preferably have 1 to 30 carbon atoms.

$B^1$ represents a substituent represented by the following General Formula (2):

[Formula 11]

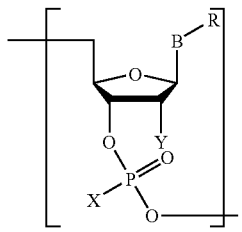

(2)

In General Formula (2), B represents a natural or non-natural nucleotide base, and examples thereof include natural adenine, cytosine, guanine, thymine, and uracil; and artificial bases such as 7-deazaadenine, 7-deaza-8-azaadenine, 3-deazaadenine, 6-thioguanine, 2-thiouracil, 2-thiothymine, 7-deazaadenine substituted by a substituent (for example, an alkyl, alkenyl, alkynyl, halogen, nitro, acyl, or hydroxyl group) at the 7-position, adenine substituted by a substituent (for example, an alkyl, alkenyl, alkynyl, halogen, nitro, acyl, or hydroxyl group) at the 8-position, 7-deazaadenine substituted by a substituent (for example, an alkyl, halogen, nitro, acyl, or hydroxyl group) at the 8-position, 7-deazaadenine, 7-deazaguanine, 7-deaza-8-azaguanine, and 3-deazaguanine substituted by substituents (for example, an alkyl, alkenyl, alkynyl, halogen, nitro, acyl, or hydroxyl group) at the 7- and 8-positions, 7-deazaguanine substituted by a substituent (for example, an alkyl, alkenyl, alkynyl, halogen, nitro, acyl, or hydroxyl group) at the 7-position, guanine substituted by a substituent (an alkyl, alkenyl, alkynyl, halogen, nitro, acyl, or hydroxyl group) at the 8-position, 7-deazaguanine substituted by a substituent (for example, an alkyl, alkenyl, alkynyl, halogen, nitro, acyl, or hydroxyl group) at the 8-position, 7-deazaguanine substituted by substituents (for example, an alkyl, alkenyl, alkynyl, halogen, nitro, acyl, or hydroxyl group) at the 7- and 8-positions, cytosine substituted by a functional group (for example, an alkyl, alkenyl, alkynyl, halogen, nitro, acyl, or hydroxyl group) at the 5-position, pseudo-isocytosine, pseudo-isocytosine substituted by a functional group (for example, an alkyl, alkenyl, alkynyl, acyl, or hydroxyl group) at the 1-position, uracil substituted by a functional group (for example, an alkyl, alkenyl, alkynyl, halogen, nitro, acyl, or hydroxyl group) at the 5-position, pseudo-uracil, and pseudo-uracil substituted by a functional group (for example, an alkyl, alkenyl, alkynyl, acyl, or hydroxyl group) at the 1-position.

R represents a substituent bound to an amino group of the nucleotide base. Therefore, when B does not have an amino group, the nucleotide base does not have $R^2$. Examples of R include hydrogen atoms, acyl groups, thioacyl groups, alkoxycarbonyl groups, alkoxythiocarbonyl groups, carbamoyl groups which may be substituted by alkyl groups, thiocarbamoyl groups which may be substituted by alkyl groups, and alkyl groups (which may be bound to alkyl groups, alkenyl groups, alkynyl groups, or phenyl groups). The alkyl groups preferably have 1 to 30 carbon atoms. In addition, the alkyl groups, the alkenyl groups, and the alkynyl groups which are bound to the alkyl groups preferably have 1 to 30 carbon atoms. The alkyl groups which are bound to the carbamoyl groups or the thiocarbamoyl groups preferably have about 1 to 10 carbon atoms.

X represents an oxygen ion, a sulfur ion, $BH_3$, $OCH_3$, or $CH_3$. Y represents a hydrogen atom, a hydroxyl group, an alkoxy group, or a 2-cyanoethoxy group ethyl group or may be bound to the carbon atom at the 4'-position of the ribose to form a ring.

Furthermore, in the above-mentioned General Formulae (1) and (2), at least one of B and $B^2$ is a nucleotide base having an amino group, and at least one of R and $R_2$ is not a hydrogen atom.

The oligonucleotide derivative according to the present invention can be used as a probe. This probe can be used for, for example, determining a base at a certain position of a target nucleic acid present in a sample.

The oligonucleotide derivative of the present invention can be prepared by a combination of known methods. The oligonucleotide derivative of the present invention can be prepared by first preparing each unit (phosphoroamidite) constituting an oligonucleotide derivative and then coupling the units. Specifically, the oligonucleotide derivative can be prepared by the method described in Examples below.

Each unit constituting the oligonucleotide derivative can be prepared by a combination of known methods. In addition, the unit (phosphoroamidite) constituting the oligonucleotide derivative may be commercially available one.

The DNA chip according to the present invention will now be described.

The DNA chip (or microarray) of the present invention includes at least one oligonucleotide derivative of the present invention described above, the oligonucleotide being immobilized. Immobilization is a concept containing adsorption and also containing bonding such as a covalent bond.

In the preparation of the DNA chip (or microarray), the diameter of a spot of DNA spotted on a substrate surface is not specifically limited, but is usually about 50 to 200 µm. In addition, the spotting pitch is not specifically limited, but is usually about 100 to 500 µm.

In the DNA chip (or microarray) according to the present invention, the oligonucleotide derivative represented by General Formula (1) is immobilized to a support via $A_1$ or $A_2$ of the oligonucleotide derivative. Examples of the support used include glass such as controlled pore glass and porous glass; and a magnetic bead being composed of a core of polystyrene, a metal, or ferrite and glycine methacrylate coating the core surface. The support may have any shape such as a plate (substrate) or a bead.

The DNA chip may a probe-on-carrier type. The probe-on-carrier is a technique for detecting SNPs by synthesizing DNA probes on controlled pore glass (CPG), which is used as a material most suitable for DNA synthesis, and using the DNA probes immobilized on the CPG without detaching the probe molecules from the CPG support. The CPG used preferably has a particle size of 500 to 5,000 Å. In this probe-on-carrier technique, since a step of immobilizing DNA probes to a substrate is not necessary, high-throughput production of DNA chips is possible. In addition, the efficiency of DNA chain elongation reaction is significantly high such as 99.8% or more. Therefore, the purity of DNA probes can be high to dramatically improve the accuracy of the DNA chips. Furthermore, CPG immobilized with necessary DNA probes can be produced in a large volume. Therefore, the manufacturing cost can be reduced and higher quality control can be performed. Furthermore, though most conventional DNA chips are used in two-dimensional detection on a slide glass surface, in the probe-on-carrier using CPG, three-dimensional detection is possible. Therefore, DNA probes can be arranged in a high density, and high-sensitive detection can be performed.

In a case that a known DNA synthesis system is applied to the above-mentioned probe-on-carrier, the Si—O bond at the linker region is cleaved during a process (treatment with ammonia) of removing a protecting group of a nucleotide base. A phenomenon that about 90% of DNA probes are released from the carrier surfaces is observed. However, in a case that an oligonucleotide derivative according to the present invention is applied to probe-on-carries, the protecting group does not require to be removed. Therefore, the above-mentioned problem does not occur.

The immobilization of the oligonucleotide derivative of the present invention onto a support surface may be performed by a method of binding $A_1$ or $A_2$ of the oligonucleotide derivative represented by General Formula (1) to the support surface via a proper linker by, for example, a metal-sulfur bond. The oligonucleotide derivative immobilized on the support surface may be not only one type but also two or more types. $A_1$ or $A_2$ not participating in the binding to the support may be bound to a fluorescent molecule, a quenching molecule, or the like which is used for detection when used as a DNA chip.

The DNA chip (or microarray) according to the present invention can be used for a method of identifying nucleic acid in a sample.

In such a method, first, a sample is applied to the DNA chip (or microarray) of the present invention for hybridization. For example, about 0.1 to 100 μM of a sample is applied to oligonucleotide derivatives immobilized to the DNA chip (or microarray). The conditions for the hybridization differ depending on types of the polynucleotide derivatives, but are, for example, at a temperature of 0 to 60° C. for about 1 to 30 hours.

After the completion of the hybridization, washing with a washing solution suitable for the type of the chip is conducted two to five times. Thus, the oligonucleotide derivative according to the present invention can be used for identification of nucleic acid or gene detection. The gene detection can be performed by real-time PCR as well as the method using a DNA chip or microarray, and the oligonucleotide derivative of the present invention can be used in such a method.

A method of identifying a nucleotide in a target nucleic acid according to the present invention will now be described.

The method of identifying a nucleotide in a target nucleic acid of the present invention includes the steps of hybridizing an oligonucleotide derivative represented by the above-mentioned General Formula (1) to a target nucleic acid in a sample; and detecting the hybridization product.

In the method of identifying a nucleotide in a target nucleic acid according to the present invention, first, an oligonucleotide derivative represented by the above-mentioned General Formula (1) is hybridized to a target nucleic acid in a sample. Any sample containing nucleic acid can be used without specific limitation, and examples thereof include cell extracts, body fluids such as blood, PCR products, and oligonucleotides. Conditions for the hybridization are the same as above.

The oligonucleotide derivative according to the present invention can be applied to a gene expression-regulating method of suppressing expression of gene. The gene expression-regulating method according to the present invention is conducted by designing an oligonucleotide derivative which can bind to a target position of a gene of which expression is regulated and administering the oligonucleotide derivative to cells. The oligonucleotide derivative may be administered alone or in a state of being immobilized on a carrier and may be orally or parenterally administered. The parenteral administration can be conducted by, for example, local intravenous, intramuscular, hypodermic, or transcutaneous administration. Furthermore, a technique for transporting an antisense oligonucleotide to target tissue or readily introducing to target cells, for example, liposome of pharmacologically acceptable cationic lipid, can be utilized. The oligonucleotide administered is bound to the target position of a gene of which expression is regulated and regulates the gene expression.

The nucleotide derivative according to the present invention will now be described.

First, a nucleotide derivative according to a first embodiment of the present invention will be described.

The nucleotide derivative according to the first embodiment of the present invention is represented by the following General Formula (17):

[Formula 12]

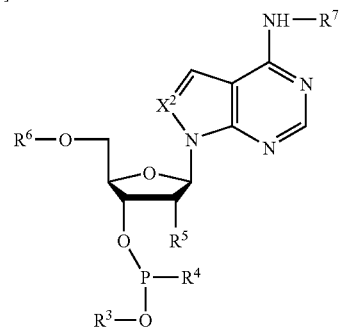

(17)

In General Formula (17), $R^3$ represents a phosphate-protecting group. Any phosphate-protecting group which is used in a phosphoroamidite method can be used without specific limitation, and examples thereof include methyl groups, 2-cyanoethyl groups, and 2-trimethylsilylethyl groups.

$R^4$ represents a dialkylamino group having the same or different two alkyl groups each having one to six carbon atoms on its nitrogen atom. The two alkyl groups may be mutually bound to form a ring. Examples of the dialkylamino group include diethylamino groups, diisopropylamino groups, and dimethylamino groups.

$R^5$ represents a hydrogen atom, an alkoxy group, or a trialkylsilyloxy group, a trialkylsilyloxymethoxy group, or a cyanoethyl group which has the same or different alkyl groups each having one to ten carbon atoms or is bound to the carbon atom at the 4'-position of the ribose to form a ring. Alkoxy groups having one to six carbon atoms are preferred, and examples thereof include methoxy groups, ethoxy groups, propoxy groups, 1-butyloxy groups, 1-pentyloxy groups, and 1-hexyloxy groups and furthermore include branched alkoxy groups such as 2-propyloxy groups and isobutyloxy groups; and alkoxy groups of which all or part of the side-chain is cyclized, such as cyclopropyloxy groups, cyclobutyloxy groups, cyclopentyloxy groups, cyclohexyloxy groups, and cyclopropylmethyloxy groups.

$R^6$ represents a hydroxyl-protecting group. Any hydroxyl-protecting group which is used in a phosphoroamidite method can be used without specific limitation, and examples thereof include dimethoxytrityl groups and monomethoxytrityl groups.

$R^7$ represents an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group). The alkyl group preferably has 1 to 30 carbon atoms. The alkyl group, the alkenyl group, and the alkynyl group which bond to the alkyl group preferably has 1 to 30 carbon atoms.

$X^2$ represents a nitrogen atom or a carbon atom which may have a substituent thereon.

Examples of the nucleotide derivative represented by General Formula (17) according to the present invention include a compound (5'-O-(4,4'-dimethoxytrityl)-2'-deoxy-6-N-acetyl-7-deazaadenosine-3'-(2-cyanoethyl-N,N-diisopropylphosphoroamidide) represented by the following Formula (20) and a compound (5'-O-(4,4'-dimethoxytrityl)-2'-deoxy-6-N-acetyl-8-aza-7-deazaadenosine-3'-(2-cyanoethyl-N,N-diisopropylphosphoroamidide) represented by the following Formula (21).

[Formula 13]

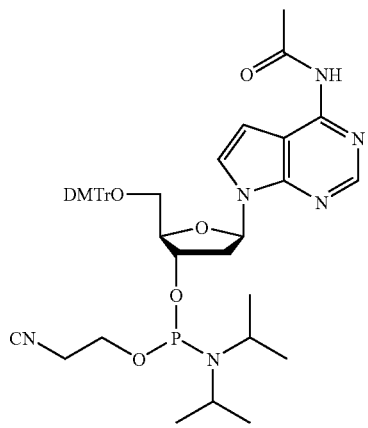
(20)

[Formula 14]

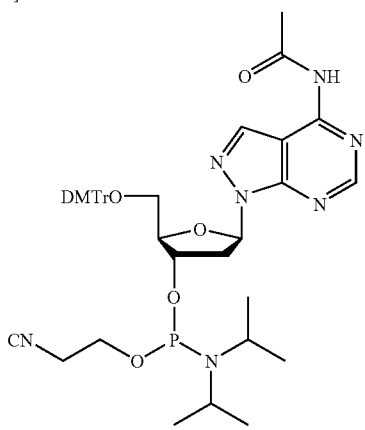
(21)

In Formulae (20) and (21), DMTr represents a dimethyltrityl group (hereinafter the same meaning in this description).

A nucleotide derivative according to a second embodiment of the present invention will now be described.

The nucleotide derivative according to the second embodiment of the present invention is represented by the following General Formula (18):

[Formula 15]

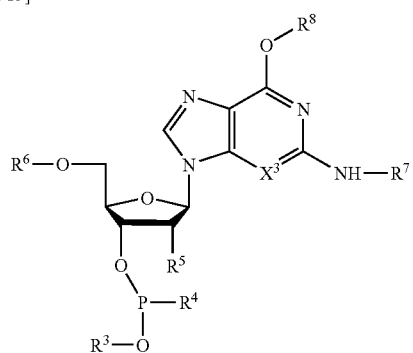
(18)

In General Formula (18), $R^3$, $R^4$, $R^5$, $R^6$, and $R^7$ are the same as those described in the above-mentioned Formula (17). $X^3$ represents a nitrogen atom or methine. The nucleotide derivative represented by General Formula (18) may have one or more diphenylcarbamoyl group. $R^8$ represents a diphenylcarbamoyl group or a silyl group having the same or different three aryl or alkyl groups in total on its silicon atom. An example of $R^8$ is t-butyldiphenylsilyl group. Examples of the nucleotide derivative represented by the above-mentioned General Formula (18) according to the present invention include a compound (5'-O-(4,4'-dimethoxytrityl)-6-O-diphenylcarbamoyl-2-N-methylcarbamoyldeoxyguanosine-3'-(2-cyanoethyl-N,N-diisopropylphosphoroamidide) represented by the following Formula (22), a compound (2-N-carbamoyl-5'-O-(4,4'-dimethoxytrityl))-6-O-diphenylcarbamoyldeoxyguanosine-3'-(2-cyanoethyl-N,N-diisopropylphosphoroamidide) represented by the following Formula (23), and a compound (5'-O-(4,4'-dimethoxytrityl)-6-O-diphenylcarbamoyl-2-N-methylthiocarbamoyldeoxyguanosine-3'-(2-cyanoethyl-N,N-diisopropylphosphoroamidide) represented by the following Formula (24).

[Formula 16]

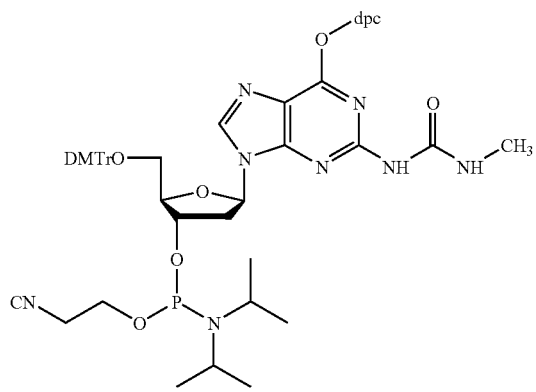
(22)

[Formula 17]

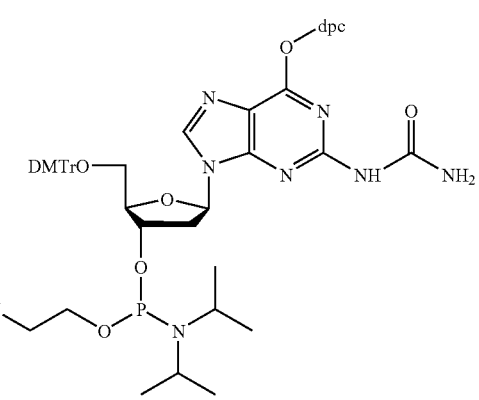
(23)

[Formula 18]

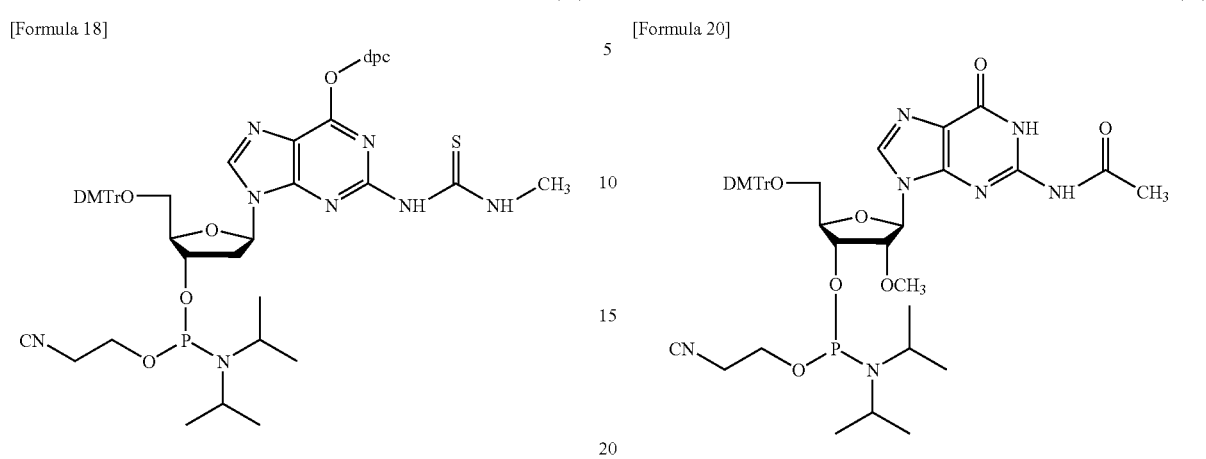

(24)

A nucleotide derivative according to a third embodiment of the present invention will now be described.

The nucleotide according to the third embodiment of the present invention is represented by the following General Formula (19):

[Formula 19]

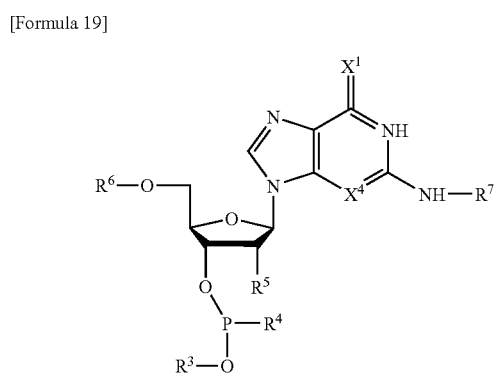

(19)

In General Formula (19), $R^3$, $R^4$, $R^5$, $R^6$, and $R^7$ are the same as those described in the above-mentioned Formula (17). In General Formula (19), X represents a nitrogen atom or methine; $X^1$ represents an oxygen atom or a sulfur atom; and $X^4$ represents a nitrogen atom or methine. The nucleotide derivative represented by General Formula (19) may have one or more diphenylcarbamoyl group. Examples of the nucleotide derivative represented by General Formula (19) according to the present invention include a compound (2-N-acetyl-5'-O-(4,4'-dimethoxytrityl)-2'-O-methyl-3-deazaguanosine-3'-(2-cyanoethyl-N,N-diisopropylphosphoroamidide) represented by the following Formula (25).

[Formula 20]

(25)

The nucleotide derivatives according to the present invention can be used as raw materials for producing the above-mentioned oligonucleotide derivatives of the present invention.

EXAMPLES

The present invention will now be described in further detail with reference to Examples, but is not limited to such Examples.

Example 1

Deoxyguanosine (1.33 g, 5 mmol) was dehydrated by azeotrope with pyridine and then dissolved in 30 mL of anhydrous methanol. After the addition of dimethoxydimethylaminomethane (1.81 mL, 1.78 g, 15 mmol), the mixture was stirred at 55° C. for 15 hours. After the completion of the stirring, the reaction solution was cooled to room temperature. The resulting precipitate was collected by filtration to give a white powder of the product. Then, the given white powder was dehydrated by azeotrope with pyridine and then dissolved in 50 mL of anhydrous pyridine. To the resulting solution, dimethoxytrityl chloride (1.86 g, 5.5 mmol) was added. The mixture was stirred at room temperature for 12 hours, and 10 mL of methanol was added to this reaction solution. The mixture was further stirred for 5 minutes. Then, this reaction solution was diluted with 200 mL of chloroform and extracted with 200 mL of a 5% by mass sodium hydrogen carbonate aqueous solution three times. The organic layers were combined, dried over anhydrous sodium sulfate, and filtered. The solvent was evaporated under reduced pressure. The resulting crude product was crystallized with diisopropyl ether and filtered to collect a white powder of the product.

Then, the obtained white powder of the product was added to 100 mL of a pyridine-ammonia aqueous solution (1:1, v/v). The mixture was stirred at room temperature for 15 hours. After the completion of the stirring, ammonia was evaporated under reduced pressure. The residue was diluted with 200 mL of chloroform and extracted with 200 mL of a 5% by mass sodium hydrogen carbonate aqueous solution three times. Then, the organic layers were combined, dried over anhydrous sodium sulfate, and filtered. The solvent was evaporated under reduced pressure. The resulting crude product was crystallized with diisopropyl ether and filtered to collect a white powder of 5'-O-(dimethoxy)trityl-2'-deoxyguanosine (1.65 g, yield: 58%).

$^1$H NMR (CDCl$_3$): 2.22-2.31 (m, 1H), 2.57-267 (m, 1H), 3.09-3.15 (m, 2H), 3.71 (s, 6H), 3.81-3.91 (m, 1H), 4.32-4.35 (m, 1H), 5.28 (d, 1H, J=4.4 Hz), 6.12 (dd, 1H, J=6.3, 6.8 Hz), 6.42 (br s, 2H), 6.81 (dd, 4H, J=6.8, 8.8 Hz), 7.17-7.34 (m, 9H), 7.76 (s, 1H), 10.58 (br s, 1H).

5'-O-(Dimethoxy)trityl-2'-deoxyguanosine (2.85 g, 5 mmol) prepared in above was dehydrated by azeotrope with pyridine, toluene, and dichloromethane in this order, and then dissolved in 10 mL of anhydrous tetrahydrofuran (THF). After the addition of diisopropylethylamine (1.23 mL, 7.5 mmol), the resulting solution was cooled to −78° C., and (2-cyanoethoxy group ethyl)-(N,N-diisopropylamino)chlorophosphine (1.23 mL, 5.5 mmol) was added thereto. The mixture was gradually returned to room temperature and stirred for 1 hour. Then, this reaction solution was poured into 20 mL of water and then diluted with 200 mL of chloroform. The mixture was extracted with 200 mL of a 5% by mass sodium hydrogen carbonate aqueous solution three times. The organic layers were combined, dried over anhydrous sodium sulfate, and filtered. The solvent was evaporated under reduced pressure. The resulting crude product was purified by silica gel chromatography (1% triethylamine) and eluted with hexane-chloroform (chloroform concentration was changed from 50% to 100%) and then with chloroform-methanol (methanol concentration was changed from 0% to 3%). The solvent was evaporated to give a white solid of 5'-O-(dimethoxy)trityl-2'-deoxyguanosine-3'-O-(2-cyanoethoxy group ethyl-N,N-diisopropylphosphoroamidite) (the compound represented by the following Formula (3), 3.35 g, yield: 92%).

$^{31}$P NMR (CDCl$_3$): 149.4, 149.2

$^1$H NMR (CDCl$_3$): 1.01-1.25 (m, 12H), 2.41 (t, 1H, J=10.5 Hz), 2.43-2.77 (m, 3H), 3.31-3.80 (m, 12H), 4.11-4.18 (m, 1H), 4.55-4.61 (m, 1H), 6.43-6.49 (m, 1H), 6.74-6.80 (m, 4H), 7.10-7.36 (m, 11H), 760-7.69 (m, 1H).

[Formula 21]

(3)

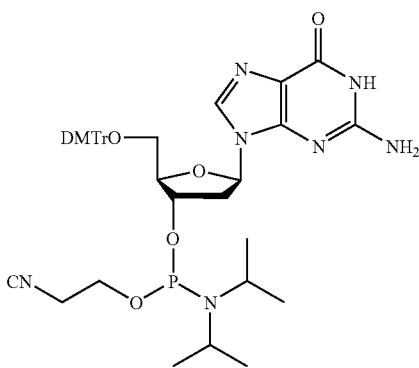

Example 2

2'-Deoxyadenosine monohydrate (4 g, 15 mmol) was suspended in 75 mL of a sodium acetate buffer solution (pH 4.3). To this suspension, 75 mL of a sodium acetate buffer solution (pH 4.3) containing bromine (0.92 mL, 18 mmol) was drop-wise added. The resulting mixture was stirred at room temperature for 2 hours, and then 50 mL of a 5% sodium thiosulfate aqueous solution and then 50 mL of a 2 M sodium hydroxide aqueous solution were added thereto. The given precipitate was collected by filtration and sufficiently washed with water and ethanol to give 8-bromo-2'-deoxyadenosine (4.2 g, yield: 83%).

$^1$H NMR (DMSO): 2.08-2.16 (m, 1H), 3.05-3.15 (m, 1H), 3.41-3.48 (m, 1H), 3.54-3.61 (m, 1H), 3.78-3.83 (m, 1H), 4.40-4.41 (m, 1H), 4.91 (s, 1H), 5.29 (s, 1H), 5.43 (br s, 2H), 6.13 (t, 1H, J=7.25 Hz), 8.12 (s, 1H).

8-Bromo-2'-deoxyadenosine (4.2 g, 12.5 mmol) prepared in above was dissolved in 80% acetic acid-acetic anhydride (1:1, v/v, 250 mL), and sodium acetate (18.5 g, 225 mmol) was added thereto. The mixture was stirred at 120° C. for 3 hours and then extracted with ethyl acetate-water (500 mL/500 mL). The organic layers were combined, and the solvent was removed under reduced pressure. The obtained crude product was dissolved in 28% aqueous ammonia-pyridine (1:1, v/v, 250 mL). The solution was stirred at room temperature for 5 hours. Then, the reaction solvent was evaporated under reduced pressure. The resulting solid was sufficiently washed with ethanol and filtered to give 2'-deoxy-7,8-dihydro-6-N-acetyladenosin-8-one (1.9 g, yield: 55%).

$^1$H NMR (DMSO): 2.05-2.12 (m, 1H), 2.21 (s, 3H), 3.03-3.16 (m, 1H), 3.45-3.48 (m, 1H), 3.55-3.60 (m, 1H), 3.78-3.80 (m, 1H), 4.38 (br s, 1H), 4.81 (br s, 1H), 5.22 (s, 1H), 6.15 (t, 1H, J=7.25 Hz), 8.12 (s, 1H), 10.20 (br s, 1H), 10.83 (br s, 1H).

2'-Deoxy-7,8-dihydro-6-N-acetyladenosin-8-one (1.5 g, 5 mmol) prepared in above was dehydrated by azeotrope with pyridine and dissolved in 50 mL of anhydrous pyridine. Then, dimethoxytrityl chloride (1.86 g, 5.5 mmol) was added to this solution. The resulting solution was stirred at room temperature for 4 hours, and then 10 mL of methanol was added thereto. The resulting mixture was further stirred for 5 minutes and then diluted with 200 mL of chloroform. The resulting mixture was extracted with 200 mL of a 5% by mass sodium hydrogen carbonate aqueous solution three times. The organic layers were combined, dried with anhydrous sodium sulfate, and filtered. The solvent was evaporated under reduced pressure. The resulting crude product was purified by silica gel chromatography and eluted with chloroform (0.5% pyridine) containing methanol gradient from 0% to 3%. The solvent was evaporated to give a white solid of 2'-deoxy-5'-O-(4,4'-dimethoxytrityl)-7,8-dihydro-6-N-acetyladenosin-8-one (2.45 g, yield: 80%).

$^1$H NMR (CDCl$_3$): 2.11-2.15 (m, 1H), 2.21 (s, 3H), 3.04-3.15 (m, 1H), 3.70 (s, 6H), 3.81-3.91 (m, 1H), 4.32-4.35 (m, 1H), 6.13 (dd, 1H, J=6.2, 6.7 Hz), 6.81 (dd, 4H, J=6.8, 8.8 Hz), 7.10-7.28 (m, 9H), 8.20 (s, 1H), 10.20 (br s, 1H), 10.82 (br s, 1H).

2'-Deoxy-5'-O-(4,4'-dimethoxytrityl)-7,8-dihydro-6-N-acetyladenosin-8-one (3.06 g, 5 mmol) prepared in above was dehydrated by azeotrope with pyridine, toluene, and dichloromethane in this order and dissolved in 10 mL of anhydrous THF. Then, diisopropylethylamine (1.23 mL, 7.5 mmol) was added thereto. The resulting solution was cooled to −78° C., and (2-cyanoethoxy group ethyl)-(N,N-diisopropylamino) chlorophosphine (1.23 mL, 5.5 mmol) was added thereto. The mixture was gradually returned to room temperature and stirred for 1 hour. Then, the reaction solution was poured into 20 mL of water and diluted with 200 mL of chloroform. The resulting mixture was extracted with 200 mL of a 5% by mass sodium hydrogen carbonate aqueous solution three times. The organic layers were combined, dried over anhydrous sodium sulfate, and filtered. The solvent was evaporated under reduced pressure. The resulting crude product was purified by silica gel chromatography (1% triethylamine) and eluted with gradient of hexane-chloroform (chloroform concentration was changed from 50% to 100%) and chloroform-methanol (methanol concentration was changed from 0 to 3%). The solvent was evaporated to give a white solid of 2'-deoxy-5'-O-(4,4'-dimethoxytrityl)-7,8-dihydro-6-N-acetyl adenosin-8-on-3'-O-(2-cyanoethoxy group ethyl)-N,N-diisopropylphosphoroamidite (compound represented by the following Formula (4), 3.57 g, yield: 88%).

[Formula 22]

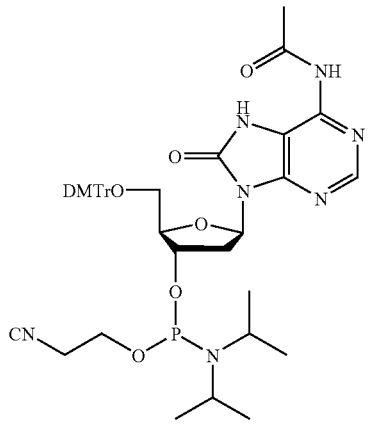

(4)

A probe was produced using a compound (phosphoroamidite) represented by the above-mentioned Formula (3), a compound (phosphoroamidite) represented by the above-mentioned Formula (4), a compound represented by the following Formula (5), and a compound represented by the following Formula (6). As the compounds represented by the following Formulae (5) and (6), commercially available ones were used. The compound represented by the following Formula (5) was available from GLEN RESERCH Co., Ltd. under trade name "P/N 10-1015-02 Ac-dC-CE Phosphoramidite", and the compound represented by the following Formula (6) was available from GLEN RESERCH Co., Ltd. under trade name "P/N 10-1030-02 dT-CE Phosphoramidite".

[Formula 23]

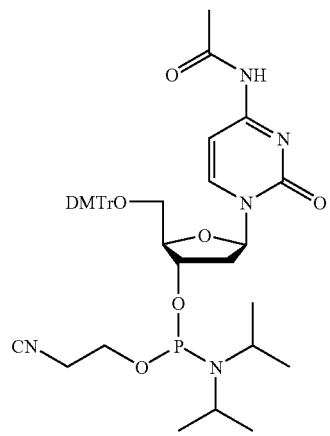

(5)

[Formula 24]

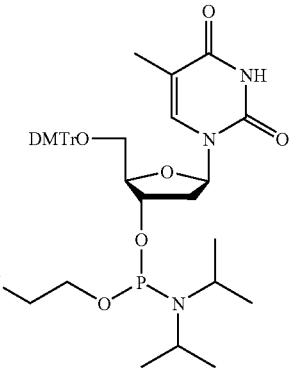

(6)

A probe having a sequence of GCCTCCGGTTCAT (SEQ ID NO: 1) was synthesized using an autosynthesizer available from Applied Biosynthesis Inc. under trade name "DNA/RNA Synthesizer 392". The synthesis of the probe with the autosynthesizer was conducted using a controlled pore glass (CPG) solid phase support (10 mg, 10 µmol/g) having 16-hydroxyhexadecanoic acid at the end. The elongation cycle of each synthetic strand was conducted as shown in Table 1. In the condensation reaction, benzoimidazolium triflate (BIT) was used.

TABLE 1

| Step | Operation | Reagent | Time |
|---|---|---|---|
| 1 | washing | $CH_3CN$ | 0.2 |
| 2 | detritylation | 3% $Cl_3CCOOH/CH_2Cl_2$ | 1.5 |
| 3 | washing | $CH_3CN$ | 0.4 |
| 4 | coupling | 0.1 M amidide + 0.2 M BIT in CH3CN | 1.0 |
| 5 | washing | $CH_3CN$ | 0.2 |
| 6 | oxidation | 0.2 M $I_2$ in Py—H2O—THF (20:2:78, v/v/v) | 0.5 |
| 7 | washing | $CH_3CN$ | 0.4 |

Then, after the elongation of the strand, a cyanoethyl group at the phosphate moiety was removed by treatment with 1,8-diazabicyclo[5,4,0]undecene (DBU)-acetonitrile (1:9, v/v) for 1 minute while a 4,4'-dimethoxytrityl group was remained at the 5'-end. Then, the 4,4'-dimethoxytrityl group was removed by treatment with a 3% trichloroacetic acid methylene chloride solution (2 mL) for 1 minute. The solid phase support was washed with methylene chloride (1 mL, 3 times), acetonitrile (1 mL, 3 times), and a 0.1 M ammonium acetate aqueous solution in this order to give CPG immobilized with probe-immobilized CPG.

The probe-immobilized CPG prepared in above was sufficiently dried. Three fluorescent oligonucleotides having a sequence of ATGAACCGGAGGC (SEQ ID NO: 2), ATGAACCAGAGGC (SEQ ID NO: 3), or ATGAACTGGAGGC (SEQ ID NO: 4) were prepared. Each of these oligonucleotides was labeled with fluorescein at the 3'-end. The above-mentioned probe-immobilized CPG was immersed in 0.25 mL of this oligonucleotide solution (250 nM oligonucleotide, 100 mM phosphate buffer, 1 M NaCl, pH 7.0) and stirred at 50° C. for 10 hours. Then, the oligonucleotide solution was removed, and 0.25 mL of a phosphate buffer (100 mM phosphate buffer, 1 M NaCl, pH 7.0) was added thereto. The mixture was stirred at 50° C. for 1 hour. Then, the phosphate buffer was removed, and the CPG was measured for fluorescence.

The measurement of fluorescence was conducted by measuring fluorescent brightness by irradiating the CPG with light of 470 to 490 nm by an incident-light fluorescence system of OLYMPUS Corp. and photographing light of 510 nm or more by a digital CCD camera (ORCA-ER) of Hamamatsu Photonics K.K. The result showed that the fluorescent brightness was high only when the oligonucleotide of SEQ ID NO: 2 was used. That is, when the exposure time was 300 µs, the average fluorescent brightness in the case of the oligonucleotide of SEQ ID NO: 2 was 2375, that in the case of the nucleotide of SEQ ID NO: 3 was 337, and that in the case of the nucleotide of SEQ ID NO: 4 was 714. Thus, high specificity of the nucleotide of SEQ ID NO: 2 was observed.

It is obvious by the above-mentioned results that the above-mentioned probe-immobilized CPG can be used for detection of gene. In particular, it was confirmed that the probe can discriminate an oligonucleotide in which only one base is different from that of others and thereby can be used for SNPs analysis.

Example 3

Seven hundred and ninety milligrams of 3-deazaguanosine (compound represented by the following Formula (7)) was azeotroped with 1 mL of anhydrous DMF and then dissolved in 20 mL of anhydrous N,N-dimethylformamide (DMF). The resulting solution was returned to room temperature, and then 1.87 mL of N,N-dimethylformamide dimethylacetal was added thereto. The mixture was stirred for 5 hours. The solvent was evaporated under reduced pressure, and then methanol was added thereto to give precipitate. This precipitate was purified by filtration and sufficiently dried to give 2-N-((dimethylamino)methylene)-3-deazaguanosine (compound represented by the following General Formula (8), 789 mg, yield: 83%).

$^1$H NMR (DMSO-d6) δ 2.9-3.1 (6H, NCH$_3$), 3.5-4.4 (5H, 2'H, 3'H, 4'H, 5'H), 5.0-6.1 (5H, 1'H, 2'OH, 3'OH, 5'OH, 3H), 7.9-8.0 (2H, 8H, NCHN), 10.6-10.7 (1H, 1H).

[Formula 25]

(7)

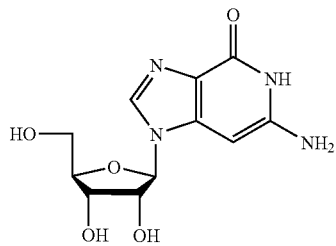

[Formula 26]

(8)

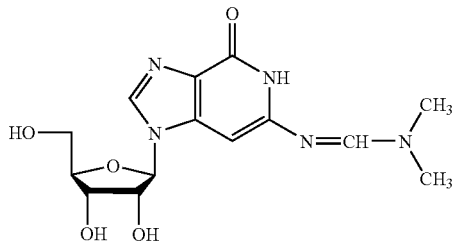

Then, the given 2-N-((dimethylamino)methylene)-3-deazaguanosine (337 mg) was azeotroped with 1 mL of anhydrous pyridine (three times) and then dissolved in 6 mL of anhydrous pyridine, and 342 µL of 1,1,3,3-tetraisopropyldisiloxane dichloride 1,3-diyl was added thereto at 0° C. The mixture was stirred for 4 hours, and then the reaction was terminated by adding 1 mL of water and 1 mL of methanol thereto. The reaction solution was extracted with 50 mL of ethyl acetate/brine (1/1) three times. The organic layer was dried over anhydrous magnesium sulfate. The solvent was evaporated under reduced pressure, and the residue was purified by silica gel column chromatography (N60: spherical neutral silica gel) with methanol/chloroform (methanol concentration was changed from 2% to 4%) to give 3',5'-O-(1,1,3,3-tetraisopropyldisiloxane-1,3-diyl)-2-N-((dimethylamino)methylene)-3-deazaguanosine (compound represented by the following Formula (9), 382 g, yield: 66%).

$^1$H NMR (DMSO-d6) δ 0.6, 1.3 (28H, CCH$_3$, SiCHC$_2$), 2.9-3.1 (6H, NCH$_3$), 3.9-4.4 (5H, 2'H, 3'H, 4'H, 5'H), 5.6-6.0 (3H, 1'H, 2'OH, 3H), 7.9-8.0 (2H, 8H, NCHN), 10.6-10.7 (1H, 1H).

[[Formula 27]]

(9)

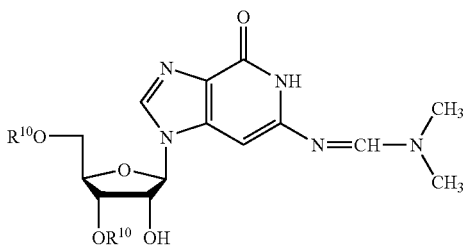

In Formula (9), R$^{10}$ represents tetraisopropyldisiloxane.

Then, 3',5'-O-(1,1,3,3-tetraisopropyldisiloxane-1,3-diyl)-2-N-((dimethylamino)methylene)-3-deazaguanosine (100 mg) prepared in above was azeotroped with 1 mL of anhydrous pyridine (three times) and dissolved in 3 mL of anhydrous pyridine, and 31 µL of isopropylethylamine and 48 mg of diphenylcarbamoyl chloride were added thereto. The mixture was stirred at room temperature for 4.5 hours, and then the reaction was terminated by adding 20 mL of sodium bicarbonate water thereto. The reaction solution was extracted with 20 mL of ethyl acetate/sodium bicarbonate water (1/1) once and then with 20 mL of ethyl acetate/brine (1/1) twice. The organic layer was dried over anhydrous magnesium sulfate, and the solvent was evaporated under reduced pressure. The residue was purified by silica gel column chromatography (N60: spherical neutral silica gel) with hexane/ ethyl acetate (hexane concentration was changed from 50% to 80%) to give 3',5'-O-(1,1,3,3-tetraisopropyldisiloxane-1,3-diyl)-6-O-diphenylcarbamoyl-2-N-((dimethylamino)methylene)-3-deazaguanosine (compound represented by the following Formula (10), 105 mg, yield: 79%).

$^1$H NMR (DMSO-d6) δ 0.6, 1.3 (28H, CCH$_3$, SiCHC$_2$), 2.9-3.1 (6H, NCH$_3$), 3.9-4.4 (5H, 2'H, 3'H, 4'H, 5'H), 5.7-5.9 (2H, 1'H, 2'OH), 6.9-7.0 (1H, 3H), 7.2-7.6 (10H, C$_6$H$_5$), 8.2-8.5 (2H, 8H, NCHN).

[Formula 28]

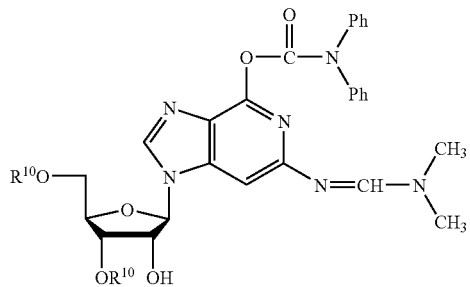

(10)

In Formula (10), R$^{10}$ represents tetraisopropyldisiloxane.

Then, 3',5'-O-(1,1,3,3-tetraisopropyldisiloxane-1,3-diyl)-6-O-diphenylcarbamoyl-2-N-((dimethylamino)methylene)-3-deazaguanosine (155 mg) prepared in above was azeotroped with 1 mL of anhydrous toluene (twice) and dissolved in 5 mL of anhydrous DMF, and 62 μL of methyl iodide and 12 mg of sodium hydride were added thereto. The mixture was stirred at −20° C. for 3 hours. Then, 50 mL of ethyl acetate was added thereto, and the mixture was poured in a phosphate buffer solution (pH 7.0) to terminate the reaction. The reaction solution was extracted with ethyl acetate/phosphate buffer solution (pH 7.0) once and then with 50 mL of ethyl acetate/brine (1/1) twice. The organic layer was dried over anhydrous magnesium sulfate, and the solvent was evaporated under reduced pressure. The residue was purified by silica gel column chromatography (N60: spherical neutral silica gel) with hexane/ethyl acetate (hexane concentration was changed from 70% to 75%) to give 2'-O-methyl-3',5'-O-(1,1,3,3-tetraisopropyldisiloxane-1,3-diyl)-6-O-diphenylcarbamoyl-2-N-((dimethylamino)methylene)-3-deazaguanosine (compound represented by the following Formula (11), 118 mg, yield: 75%).

$^1$H NMR (DMSO-d6) δ 0.6, 1.3 (28H, CCH$_3$, SiCHC$_2$), 2.9-3.1 (6H, NCH$_3$), 3.5-3.6 (3H, OCH$_3$), 3.9-4.6 (5H, 2'H, 3'H, 4'H, 5'H), 6.0-6.1 (1H, 1'H), 6.8-6.9 (1H, 3H), 7.2-7.6 (10H, C$_6$H$_5$), 8.2-8.5 (2H, 8H, NCHN).

[Formula 29]

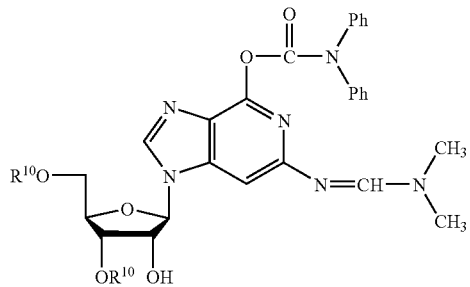

(11)

In the above-mentioned Formula (11), R$^{10}$ represents tetraisopropyldisiloxane.

Then, 2'-O-methyl-3',5'-O-(1,1,3,3-tetraisopropyldisiloxane-1,3-diyl)-6-O-diphenylcarbamoyl-2-N-((dimethylamino)methylene)-3-deazaguanosine (70 mg) prepared in above was azeotroped with 1 mL of anhydrous tetrahydrofuran (THF) (twice) and dissolved in 2.2 mL of anhydrous THF, and 36 μL of triethylamine 3 hydrogen fluoride was added thereto. The mixture was stirred at room temperature for 3 hours. Then, the solvent was evaporated under reduced pressure. The residue was purified by silica gel column chromatography (N60: spherical neutral silica gel) with ethyl acetate/methanol (ethyl acetate concentration was changed from 2% to 4%) to give 2'-O-methyl-6-O-diphenylcarbamoyl-2-N-((dimethylamino)methylene)-3-deazaguanosine (compound represented by the following Formula (12), 41 mg, yield: 83%).

If the compound was crystallized in the column, the silica gel was collected after removing by-product materials with ethyl acetate/methanol (ethyl acetate concentration was changed from 2% to 4%) and stirred in a solution of water/methanol (1:1, v/v) at room temperature for 1 hour. Then, the silica gel was removed by filtration, and the filtrate was concentrated under reduced pressure and extracted with aqueous phase/chloroform 30 times. The organic layer was dried over anhydrous magnesium sulfate, and the solvent was evaporated under reduced pressure to give 2'-O-methyl-6-O-diphenylcarbamoyl-2-N-((dimethylamino)methylene)-3-deazaguanosine.

$^1$H NMR (DMSO-d6) δ 2.9-3.1 (6H, NCH$_3$), 3.2-3.4 (3H, OCH$_3$), 3.5-4.4 (5H, 2'H, 3'H, 4'H, 5'H), 5.1-5.4 (2H, 3'OH, 5'OH), 5.9-6.0 (1H, 1'H), 6.9-7.1 (1H, 3H), 7.2-7.6 (10H, C$_6$H$_5$), 8.3-8.5 (2H, 8H, NCHN).

[Formula 30]

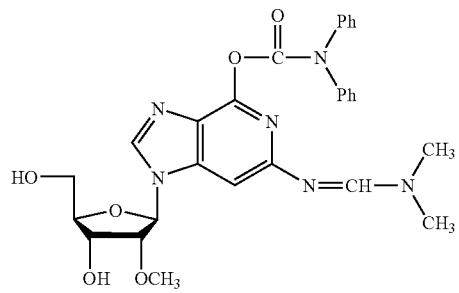

(12)

2'-O-Methyl-6-O-diphenylcarbamoyl-2-N-((dimethylamino)methylene)-3-deazaguanosine (37 mg) prepared in above was azeotroped with 1 mL of anhydrous pyridine (three times) and dissolved in 800 μL of anhydrous pyridine, and 27.5 mg of 4,4'-dimethoxytrityl chloride was added thereto. The mixture was stirred at room temperature for 3 hours. Then, the reaction was terminated by adding 20 mL of sodium bicarbonate water (concentration: 5% by mass) thereto. The reaction solution was extracted with 40 mL of ethyl acetate/sodium bicarbonate water (1/1) once and then with 40 mL of ethyl acetate/brine (1/1) twice. The organic layer was dried over anhydrous magnesium sulfate, and the solvent was evaporated under reduced pressure. The residue was purified by silica gel column chromatography (N60: spherical neutral silica gel) with hexane/ethyl acetate containing 1% triethylamine (hexane concentration was changed from 60% to 80%) to give 2'-O-methyl-5'-O-(4,4'-dimethoxytrityl)-6-O-diphenylcarbamoyl-2-N-((dimethylamino)methylene)-3- deazaguanosine (compound represented by the following Formula (13), 33 mg, yield: 57%).

$^1$H NMR (DMSO-d6) δ 2.8-3.1 (6H, NCH$_3$), 3.1-3.3 (2H, 5'H), 3.3-3.4 (3H, OCH$_3$), 3.6-3.7 (6H, OCH$_3$), 4.0-4.4 (3H, 2'H, 3'H, 4'H), 5.2-5.4 (1H, 3'OH), 5.9-6.1 (1H, 1'H), 6.7-7.6 (24H, 3H, C$_6$H$_4$, C$_6$H$_5$), 8.2-8.4 (2H, 8H, NCHN).

[Formula 31]

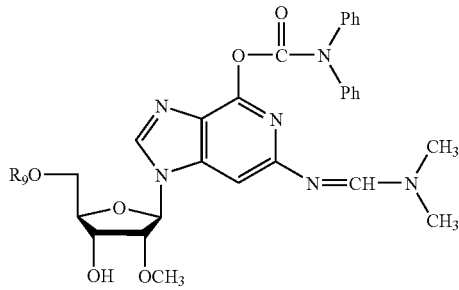

(13)

In Formula (13), R$^9$ represents 4,4'-dimethoxytrityl group.

2'-O-Methyl-5'-O-(4,4'-dimethoxytrityl)-6-O-diphenyl-carbamoyl-2-N-((dimethylamino)methylene)-3-deazaguanosine (290 mg) prepared in above was dissolved in 3.5 mL of a mixture solution of 28% aqueous ammonia: 40% methylamine:pyridine (2:2:1). The resulting solution was stirred at 50° C. for 6 hours. The solvent was evaporated under reduced pressure, and the residue was purified by silica gel column chromatography (N60: spherical neutral silica gel) with hexane/ethyl acetate (1/1) containing 1% triethylamine to give 2'-O-methyl-5'-O-(4,4'-dimethoxytrityl)-3-deazaguanosine (compound represented by the following Formula (14), 50 mg, yield: 74%).

[Formula 32]

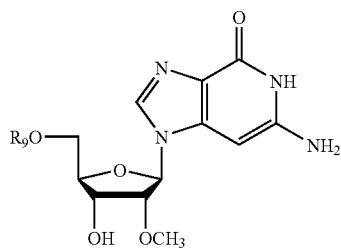

(14)

In Formula (14), R$^9$ represents 4,4'-dimethoxytrityl group.

2'-O-Methyl-5'-O-(4,4'-dimethoxytrityl)-3-deazaguanosine (18 mg) prepared in above was azeotroped with 1 mL of anhydrous pyridine (three times) and dissolved in 300 μL of acetonitrile, and 31 μL of hexamethyldisilazane was added thereto at room temperature. The mixture was stirred for 2 hours. The solvent was evaporated under reduced pressure. The residue was dissolved in 300 μL of anhydrous pyridine, and 8 μL of acetyl chloride was added thereto at 0° C. The mixture was returned to room temperature and stirred for 3 hours. Then, the reaction was terminated by adding 1 mL of water thereto. After the addition of 500 μL of aqueous ammonia, the mixture was stirred for 15 minutes and extracted with 40 mL of ethyl acetate/brine (1/1) twice. The organic layer was dried over anhydrous magnesium sulfate, and the solvent was evaporated under reduced pressure. The residue was purified by silica gel column chromatography (N60: spherical neutral silica gel) with hexane/ethyl acetate (1/1) containing 1% triethylamine to give 2'-O-methyl-5'-O-(4,4'-dimethoxytrityl)-2-N-acetyl-3-deazaguanosine (compound represented by the following Formula (15), 14.3 mg, yield: 70%).

[Formula 33]

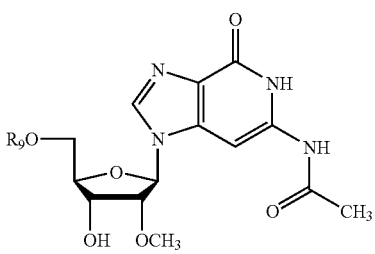

(15)

In Formula (15), R$^9$ represents 4,4'-dimethoxytrityl group.

2'-O-Methyl-5'-O-(4,4'-dimethoxytrityl)-2-N-acetyl-3-deazaguanosine (599 mg) prepared in above was azeotroped with 1 mL of anhydrous toluene (three times) and dissolved in 10 mL of anhydrous methylene chloride, and 260 μL of isopropylethylamine and 230 μL of 2-cyanodiisopropylphosphoroamidochloridite were added thereto. The mixture was stirred at room temperature for 4.5 hours. Then, 1 mL of water was added thereto to terminate the reaction. The reaction solution was extracted with 200 mL of methylene chloride/ 5% sodium bicarbonate water (1:1) five times. The organic layer was dried over anhydrous sodium sulfate, and the solvent was evaporated under reduced pressure. The residue was purified by silica gel column chromatography (N60: spherical neutral silica gel) with hexane/chloroform containing 1% triethylamine (hexane concentration was changed from 50% to 80%) to give 2'-O-methyl-3'-O-(2-cyanoethoxy group ethyl-N,N'-diisopropylphosphoroamidite)-5'-O-(4,4'-dimethoxytrityl)-2-N-acetyl-3-deazaguanosine (compound represented by the following Formula (16), 460 mg, yield: 62%).

[Formula 34]

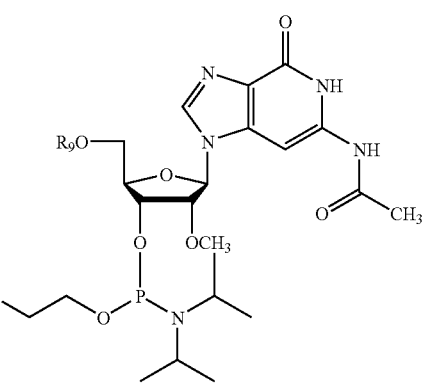

(16)

In Formula (16), R$^9$ represents 4,4'-dimethoxytrityl group.

Example 4

2'-Deoxy-7-deaza-adenosine (1 g, 4 mmol) was dehydrated by azeotrope with anhydrous pyridine three times and then dissolved in anhydrous pyridine (40 mL). To this solution, triethylamine (559 μL, 4 mmol), dichloroacetic acid (329 μL, 4 mmol), and 4,4'-dimethoxytrityl chloride (1.48 g, 4.4 mmol) were added in this order. The mixture was stirred at room temperature for 4 hours. Then, the reaction solution was diluted with CHCl$_3$ (80 mL). The CHCl$_3$ layer was washed with saturated brine three times, dried over anhydrous sodium sulfate, and filtered. The solvent was evaporated under reduced pressure to give a crude product. The obtained crude product was purified by silica gel column chromatography (20 g, 1% pyridine) and eluted with hexane containing chloroform gradient from 50% to 100% and then chloroform containing methanol gradient from 0 to 3%. Then, the solvent was evaporated to give a target solid (5'-O-(4,4'-dimethoxytrityl)-2'-deoxy-7-deaza-adenosine, 1.5 g, 68%).

$^1$H NMR (CDCl$_3$) δ 2.31-2.49 (m, 2H), 2.25 (s, 1H), 3.66 (s, 6H), 4.08 (d, 1H, 2.97 Hz), 4.54-4.56 (m, 1H), 5.55 (br s, 2H), 6.19 (d, 1H, J=4.1 Hz), 6.66 (d, 4H, J=8.9 Hz), 7.05-7.22 (m, 9H), 7.33 (d, 2H, J=1.4 Hz), 8.13 (s, 1H), 8.46 (d, 1H, J=4.3 Hz); $^{13}$C NMR (CDCl$_3$) δ 40.8, 55.2, 64.1, 72.2, 83.4, 85.6, 86.4, 99.1, 103.6, 113.6, 121.9, 123.9, 125.3, 126.9, 127.9, 128.3, 129.1, 130.1, 135.9, 136.3, 144.7, 149.6, 150.3, 151.5, 156.9, 158.5.

5'-O-(4,4'-Dimethoxytrityl)-2'-deoxy-7-deaza-adenosine (1.37 g, 2.5 mmol) prepared in above was dehydrated by azeotrope with anhydrous pyridine three times and then dissolved in anhydrous pyridine (25 mL), and trimethylsilyl chloride (935 μL, 7.45 mmol) was added thereto. The mixture was stirred at room temperature for 30 minutes. After addition of acetyl chloride (531 μL, 7.45 mmol), the mixture was further stirred for 3.5 hours. Then, 28% aqueous ammonia (12 mL) was added to this reaction solution, and the mixture was stirred for 10 minutes and diluted with CHCl$_3$ (50 mL). The organic layer was washed with saturated brine three times, dried over anhydrous sodium sulfate, and filtered. The solvent was evaporated under reduced pressure, and the resulting crude product was purified by silica gel column chromatography (25 g, 1% pyridine) and eluted with hexane containing chloroform gradient from 50% to 100% and then chloroform containing methanol gradient from 0 to 3%. Then, the solvent was evaporated to give a target solid (5'-O-(4,4'-dimethoxytrityl)-2'-deoxy-6-N-acetyl-7-deazaadenosine, 1.4 g, 95%).

$^1$H NMR (CDCl$_3$): 2.30 (s, 3H), 2.39-2.46 (m, 1H), 2.52-2.57 (m, 1H), 3.33-3.39 (m, 2H), 3.75 (s, 6H), 4.06 (d, 1H, 4.3 Hz), 4.59 (dd, 1H, 6.2 Hz, 9.9 Hz), 6.77 (d, 4H, J=8.6 Hz), 6.86 (d, 1H, J=4.1 Hz), 7.18-7.31 (m, 9H), 7.39 (d, 2H, J=6.75 Hz), 8.46 (s, 1H), 8.63 (s, 1H); $^{13}$C NMR (CDCl$_3$): 24.6, 40.4, 55.2, 63.9, 72.7, 77.2, 83.1, 85.2, 86.6, 108.6, 113.2, 123.5, 126.9, 127.9, 128.1, 130.0, 135.6, 135.7, 144.5, 149.9, 150.3, 158.5.

5'-O-(4,4'-Dimethoxytrityl)-2'-deoxy-6-N-acetyl-7-deazaadenosine (1.4 g, 2.4 mmol) prepared in above was dehydrated by azeotrope with anhydrous acetonitrile three times and then dissolved in anhydrous dichloromethane (25 mL). To the resulting solution, ethyldiisopropylamine (575 μL, 3.5 mmol) and chloro(2-cyanoethoxy)-(N,N'-diisopropylamino)phosphine (571 μL, 2.6 mmol) were added in this order. The mixture was stirred at room temperature for 30 minutes, and then water (1 mL) was added to this reaction solution. The mixture was stirred for 5 minutes and then diluted with CHCl$_3$ (25 mL). The organic layer was washed with saturated brine three times, dried over anhydrous sodium sulfate, and filtered. The solvent was evaporated under reduced pressure to give a crude product. The resulting crude product was purified by silica gel column chromatography (25 g, 1% triethylamine) and eluted with hexane containing chloroform gradient from 50% to 100% and then chloroform containing methanol gradient from 0 to 3%. The solvent was evaporated to give a target solid (compound represented by the following Formula (20), 5'-O-(4,4'-dimethoxytrityl)-2'-deoxy-6-N-acetyl-7-deazaadenosine-3'-(2-cyanoethyl-N,N-diisopropylphosphoroamidite, 1.7 g, 91%).

$^1$H NMR (CDCl$_3$): 1.01-1.12 (m, 12H), 2.36 (s, 3H), 2.39 (t, 1H, J=6.8 Hz), 3.23-3.27 (m, 2H), 3.49-4.16 (m, 10H), 4.16 (s, 1H), 4.65 (s, 1H), 6.77 (dd, 4H, J=4.3 Hz, J=7.8 Hz), 6.81 (d, 1H, J=3.2 Hz), 7.11-7.36 (m, 11H), 8.43 (s, 1H), 9.37 (s, 1H); $^{13}$C NMR (CDCl$_3$): 20.1, 20.2, 20.3, 20.4, 22.8, 24.5, 24.6, 24.7, 29.7, 39.8, 43.1, 43.1, 43.3, 43.3, 55.2, 58.1, 58.2, 58.4, 58.5, 63.4, 63.6, 68.3, 73.3, 73.6, 73.9, 74.2, 77.3, 83.4, 84.9, 85.0, 85.1, 85.2, 86.4, 104.2, 109.0, 113.1, 117.4, 117.5, 123.7, 126.9, 127.8, 128.2, 128.2, 130.1, 130.5, 135.7, 135.7, 144.6, 150.2, 152.8, 152.8, 158.5, 169.0; $^{31}$P NMR (CDCl$_3$): 149.2, 149.4.

[Formula 35]

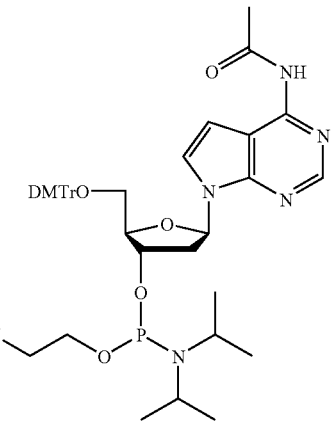

(20)

Example 5

5',3'-Bistoluoyl-2'-deoxy-6-chloro-7-deazapurine (2.0 g, 4 mmol) was dissolved in saturated ammonia-MeOH (40 mL). The resulting solution was placed in a sealable container and stirred at 60° C. for 3 days in a sealed condition. Then, the solvent was evaporated under reduced pressure, and the residue was extracted with diethyl ether (50 mL) and water (40 mL). The aqueous layers were combined, and the solvent was evaporated under reduced pressure. The residue was dehydrated by azeotrope with anhydrous pyridine three times and then dissolved in anhydrous pyridine (40 mL). To this solution, triethylamine (559 μL, 4 mmol), dichloroacetic acid (329 μL, 4 mmol), and 4,4'-dimethoxytrityl chloride (1.48 g, 4.4 mmol) were added in this order. The mixture was stirred at room temperature for 4 hours. Then, the reaction solution was diluted with CHCl$_3$ (80 mL). The CHCl$_3$ layer was washed with saturated brine three times, dried over anhydrous sodium sulfate, and filtered. The solvent was evaporated under reduced pressure to give a crude product. The obtained crude product was purified by silica gel column chromatography (20 g, 1% pyridine) and eluted with hexane containing chloroform gradient from 50% to 100% and then chloroform containing methanol gradient from 0 to 3%. Then, the solvent was evaporated to give a target solid (5'-O-(4,4'-dimethoxytrityl)-2'-deoxy-8-aza-7-deaza-adenosine, 1.9 g, 85%).

$^1$H NMR (CDCl$_3$): 2.35-2.49 (m, 1H), 3.02-3.11 (m, 1H), 3.22 (dd, 1H, J=6.2 Hz, J=9.2 Hz), 3.32 (dd, 1H, J=5.1 Hz,

J=9.7 Hz), 3.79 (s, 6H), 4.03 (dd, 1H, J=5.1 Hz, J=11.1 Hz), 4.86 (dd, 1H, J=6.1 Hz, J=11.5 Hz), 5.55 (br s, 2H), 6.73 (d, 4H, J=8.1 Hz), 6.76-6.83 (m, 1H), 7.16-7.34 (m, 9H), 7.39 (d, 2H, J=1.6 Hz), 7.82 (s, 1H), 8.38 (s, 1H); $^{13}$C NMR (CDCl$_3$): 21.2, 38.0, 54.9, 64.2, 72.3, 77.2, 84.0, 85.6, 86.0, 100.9, 112.8, 123.8, 125.1, 126.5, 127.5, 127.6, 127.7, 128.0, 128.0, 129.0, 129.9, 132.0, 135.9, 136.3, 144.7, 149.0, 153.8, 155.3, 157.4, 158.1, 158.2, 158.3.

5'-O-(4,4'-Dimethoxytrityl)-2'-deoxy-8-aza-7-deaza-adenosine (1.62 g, 2.9 mmol) prepared in above was dehydrated by azeotrope with anhydrous pyridine three times and then dissolved in anhydrous pyridine (30 mL). Trimethylsilyl chloride (2.97 mL, 8.8 mmol) was added to the resulting solution, and the mixture was stirred at room temperature for 30 minutes. After addition of acetyl chloride (627 μL, 8.8 mmol), the mixture was further stirred for 3.5 hours. Then, 28% aqueous ammonia (15 mL) was added to the reaction solution, and the mixture was stirred for 10 minutes and then diluted with CHCl$_3$ (60 mL). The organic layer was washed with saturated brine three times, dried over anhydrous sodium sulfate, and filtered. The solvent was evaporated under reduced pressure to give a crude product. The resulting crude product was purified by silica gel column chromatography (25 g, 1% pyridine) and eluted with hexane containing chloroform gradient from 50% to 100% and then chloroform containing methanol gradient from 0 to 3%. Then, the solvent was evaporated to give a target solid (5'-O-(4,4'-dimethoxytrityl)-2'-deoxy-6-N-acetyl-8-aza-7-deazaadenosine, 1.4 g, 85%).

$^1$H NMR (CDCl$_3$): 2.30 (s, 3H), 2.38-2.48 (m, 1H), 3.01-3.10 (m, 1H), 3.20-3.35 (m, 2H), 3.76 (s, 6H), 4.06 (dd, 1H, J=5.1 Hz, J=11.3 Hz), 4.84 (m, 1H), 6.72-6.83 (m, 5H), 7.15-7.35 (m, 9H), 7.36 (d, 2H, J=6.48 Hz), 8.22 (s, 1H), 8.56-8.65 (s, 2H).

5'-O-(4,4'-Dimethoxytrityl)-2'-deoxy-6-N-acetyl-8-aza-7-deazaadenosine (560 mg, 0.9 mmol) prepared in above was dehydrated by azeotrope with anhydrous acetonitrile three times and then dissolved in anhydrous dichloromethane (10 mL). To the resulting solution, ethyldiisopropylamine (230 μL, 1.4 mmol) and chloro(2-cyanoethoxy)-(N,N'-diisopropylamino)phosphine (228 μL, 1.0 mmol) were added in this order. The mixture was stirred at room temperature for 30 minutes, and water (1 mL) was added thereto. The mixture was stirred for 5 minutes and diluted with CHCl$_3$ (20 mL). The organic layer was washed with saturated brine three times, dried over anhydrous sodium sulfate, and filtered. The solvent was evaporated under reduced pressure to give a crude product. The obtained crude product was purified by silica gel column chromatography (25 g, 1% triethylamine) and eluted with hexane containing chloroform gradient from 50% to 100% and then chloroform containing methanol gradient from 0 to 3%. Then, the solvent was evaporated to give a target solid (compound represented by the following Formula (21), 5'-O-(4,4'-dimethoxytrityl)-2'-deoxy-6-N-acetyl-8-aza-7-deazaadenosine-3'-(2-cyanoethyl-N,N-diisopropylphosphoroamidite, 672 mg, 90%).

$^1$H NMR (CDCl$_3$): 1.07-1.28 (m, 12H), 2.30 (s, 3H), 2.42-2.62 (m, 3H), 3.14-3.29 (m, 3H), 3.56-3.81 (m, 10H), 4.22 (s, 1H), 4.82-4.97 (m, 1H), 6.67-6.73 (m, 4H), 6.83 (t, 1H, J=4.1 Hz), 7.12-7.37 (m, 11H), 8.22 (s, 1H), 8.56 (s, 1H), 8.58 (s, 1H); $^{31}$P NMR (CDCl$_3$): 149.2, 149.4.

[Formula 36]

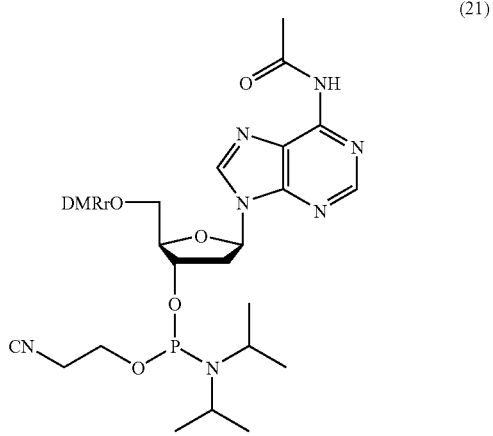

(21)

Example 6

A probe was synthesized using a compound represented by the above-mentioned Formula (20) or (21) prepared in Example 4, a compound represented by the above-mentioned Formula (3), a compound represented by the above-mentioned Formula (5), and a compound represented by the above-mentioned Formula (6) prepared in Example 5.

The synthesis of the probe was conducted using an autosynthesizer available from Applied Biosynthesis Inc. under trade name "DNA/RNA Synthesizer 392" to give a probe having a sequence of TACCTAXATACCATA (SEQ ID NO: 5, X represents deoxy-6-N-acetyl-7-deazaadenosine (in a case using a compound represented by Formula (20)) or 2'-deoxy-6-N-acetyl-8-aza-7-deazaadenosine (in a case using a compound represented by Formula (21)). In the synthesis of a probe using the autosynthesizer, a solid phase support of highly cross-linked polystyrene (HCP) having thymidine bound via a silyl linker (1 μmol, 24 μmol/g) was used. The elongation cycle of each synthetic strand was conducted as shown in Table 2. The condensation reaction was conducted using 6-nitro-1-hydroxybenzotriazole (Ho"Bt) and benzoimidazolium triflate (BIT).

TABLE 2

| Step | Operation | Reagent | Time |
|---|---|---|---|
| 1 | washing | CH$_3$CN | 0.2 |
| 2 | detritylation | 3% Cl$_3$CCOOH/CH$_2$Cl$_2$ | 1.5 |
| 3 | washing | CH$_3$CN | 0.4 |
| 4 | coupling | 0.1 M amidide + 0.1 M Ho"Bt in + BIT in CH$_3$CN | 1.0 |
| 5 | washing | CH$_3$CN | 0.2 |
| 6 | coupling | 0.1 M amidide + 0.1 M Ho"Bt in + BIT in CH$_3$CN-NMP (15:1, v/v) | 1.0 |
| 7 | washing | CH$_3$CN | 0.2 |
| 8 | oxidation | 0.2 M I2 in Py—H$_2$O—THF (20:2:78, v/v/v) | 0.5 |
| 9 | washing | CH$_3$CN | 0.4 |

Then, the DMTr group was removed with 2 mL of a 3% trichloroacetic acid solution (CH$_2$Cl$_2$). The solid phase support was washed with 1 mL of CH$_2$Cl$_2$ three times and then with 1 mL of CH$_3$CN three times. Then, the cyanoethyl group was removed using a CH$_3$CN solution (500 μL) containing 10% diazabicycloundecene (DBU). The solid phase support was washed with CH$_3$CN (1 mL×3) and then treated with a reaction solution prepared by dissolving TBAF (131 mg, 0.5 mmol) and acetic acid (24 µL, 0.5 mmol) in 500 µL of anhydrous THF for 1 hour to cut out a DNA oligomer. The resulting mixture solution was desalted using a Sep-Pak C18 cartridge and further diluted with water, and then subjected to purification by anion exchange HPLC.

The oligonucleotides having a base sequence represented by SEQ ID NO: 5 prepared in above were investigated for their double strand-forming ability and base-discriminating ability. As a control, a nucleotide having a base sequence represented by SEQ ID NO: 5 in which X is adenine was used. Oligonucleotides having a strand (ATGGTGTYTAGGTA, SEQ ID NO: 6, Y is thymidine, 2'-deoxycytidine, 2'-deoxyadenosine, or 2'-deoxyguanosine) complementary to the above-mentioned oligonucleotides were separately synthesized and mixed with the above-mentioned oligonucleotides. The mixtures were each dissolved in 500 µL of a phosphate buffer (150 mM sodium phosphate, pH 7.0, 0.1 M NaCl, 0.1 mM EDTA) so that the concentration of a double strand formed in the solution became 2 µl. The thus adjusted measurement sample was subjected to measurement using Pharma Spec UV-1700 (manufactured by Shimadzu Corp.). The measurement was conducted by first maintaining the sample at 80° C. for 30 minutes for converting the oligonucleotides to a random coil state, then decreasing the temperature of the sample to 5° C. at a rate of 1.0° C./min for annealing, and then increasing the temperature at a rate of 1.0° C./min while measuring UV absorbance at each increase of 1.0° C.

The UV absorbances obtained in the measurement were plotted against changes in temperature to obtain a double strand melting curve. The melting curve was smoothed using the Stavilzky-Golay method (25 points), and then the curve was first differentiated to determine the inflection point as a double strand melting temperature (Tm value). If a difference of 1.0° C. or more was observed between a value obtained from the curve when the double strand was annealed and a value obtained from the curve obtained when the double strand was melted, it was determined that the equilibrium of the system at each measurement temperature was incomplete, and conditions were changed, for example, by changing the rate for changing temperature to 0.5° C./min, and the measurement was conducted again. In addition, in order to investigate base-discriminating ability, the temperature for melting a double strand with an oligonucleotide having a single base-mismatching sequence. The measurement was conducted using 2.0 µM of each oligonucleotide in a 150 mM sodium phosphate buffer solution (pH 7.0) containing 0.1 M NaCl and 0.1 mM EDTA.

The results of the measurements are shown in Table 3. In the table, ΔTm means a difference between Tm in a case that a complementary strand has thymidine at the position of Y in SEQ ID NO: 6 and Tm in a case that a complementary strand has 2'-deoxyadenosine, which is the most stable mismatching.

TABLE 3

| X | Y | Tm(° C.) | ΔTm(° C.) |
|---|---|---|---|
| A | T | 45 | — |
| A | G | 32 | −13 |
| A | C | 26 | −19 |
| A | A | 29 | −16 |
| Example 4 | T | 43 | — |
| Example 4 | G | 32 | −11 |
| Example 4 | C | 24 | −19 |
| Example 4 | A | 27 | −16 |
| Example 5 | T | 45 | — |
| Example 5 | G | 31 | −14 |
| Example 5 | C | 26 | −19 |
| Example 5 | A | 29 | −16 |

The followings are confirmed by the results shown in Table 3.

The Tm of the oligonucleotide (produced from a compound prepared in Example 5) containing a base sequence represented by SEQ ID NO: 5 in which X was 2'-deoxy-6-N-acetyl-8-aza-7-deazaadenosine (8aza7deazaA) with the complementary strand represented by SEQ ID NO: 6 in which Y was thymidine was equivalent to that (45° C.) of the oligonucleotide containing 2'-deoxy-adenosine (A) at the X position. In addition, the Tm of the oligonucleotide (Example 4) containing a base sequence represented by SEQ ID NO: 5 in which X is 2'-deoxy-6-N-acetyl-8-aza-7-deazaadenosine (8aza7deazaA) with the complementary strand represented by SEQ ID NO: 6 in which Y was thymidine was equivalent to that (45° C.) of the oligonucleotide (Example 5) containing 2'-deoxy-adenosine (A) at the X position. On the other hand, in the case that the complementary strand represented by SEQ ID NO: 6 in which Y was 2'-deoxyadenosine which was the most stable mismatching, the Tm (31° C.) of the oligonucleotide containing 8aza7deazaA at the X position of the base sequence represented by SEQ ID NO: 5 was lower than that (32° C.) of the oligonucleotide containing A at the X position by 1° C. It is obvious by this result that mismatching base-discriminating ability of the oligonucleotide containing 8aza7deazaA was enhanced.

Example 7

An oligonucleotide having a sequence, TA*C*C*TA*A*A*TA*C*C*A*TA* (SEQ ID NO: 7, A* represents 2'-deoxy-6-N-acetyl-8-aza-7-deazaadenosine, and C* represents 2'-deoxy-4-N-acetylcytidine), was obtained by the same procedure as in Example 6 except that the elongation cycle of each synthetic strand was conducted as shown in Table 4 using the compound (represented by Formula (21)) obtained in Example 5 and 2'-deoxy-4-N-acetylcytidine.

TABLE 4

| Step | Operation | Reagent | Time |
|---|---|---|---|
| 1 | washing | CH$_3$CN | 0.2 |
| 2 | detritylation | 3% Cl$_3$CCOOH/CH$_2$Cl$_2$ | 1.5 |
| 3 | washing | CH$_3$CN | 0.4 |
| 4 | coupling | 0.1 M amidite + 0.2 M BIT in CH$_3$CN-NMP (15:1, v/v) | 1.0 |
| 5 | washing | CH$_3$CN | 0.2 |
| 6 | coupling | 0.1 M amidite + 0.2 M BIT in CH$_3$CN-NMP (15:1, v/v) | 1.0 |
| 7 | washing | CH$_3$CN | 0.2 |
| 8 | oxidation | 0.2 M I$_2$ in Py—H$_2$O—THF (20:2:78, v/v/v) | 0.5 |
| 9 | washing | CH$_3$CN | 0.4 |

Then, the DMTr group was removed with 2 mL of a 3% trichloroacetic acid solution (CH$_2$Cl$_2$). The solid phase support was washed with 1 mL of CH$_2$Cl$_2$ three times and then with 1 mL of CH$_2$CN three times. Then, the cyanoethyl group was removed using a CH$_3$CN solution (500 µL) containing 10% diazabicycloundecene (DBU). The solid phase support was washed with CH$_3$CN (1 mL×3) and then treated with a reaction solution prepared by dissolving TBAF (131 mg, 0.5 mmol) and acetic acid (24 μL, 0.5 mmol) in 500 μL of anhydrous THF for 1 hour to cut out a DNA oligomer. The resulting mixture solution was desalted using Sep-Pak C18 cartridge and further diluted with water, and then subjected to purification by anion exchange HPLC.

Example 8

Melting temperatures of double strands of the oligonucleotide prepared in Example 7 and its complementary oligonucleotides having a sequence (ATGGTGTYTAGGTA, SEQ ID NO: 8, Y represents any one of thymidine, 2'-deoxycytidine, 2'-deoxyadenosine, and 2'-deoxyguanosine) were measured as in Example 6. In addition, the base-discriminating ability was investigated as in Example 6. As a control, the same experiment was conducted using oligonucleotides (a compound (represented by Formula (21)) prepared in Example 5 and an oligonucleotide prepared without using 2'-deoxy-4-N-acetylcytidine, namely, an unmodified oligonucleotide).

The results are not shown in the drawings, but were that the double strand-forming ability was increased by +15.2° C. and $\Delta Tm_{A-G}$ was 17.5° C. when the oligonucleotide prepared in Example 7 was used. On the other hand, in the oligonucleotide used as the control, $\Delta Tm_{A-G}$ was 12.7° C. Thus, it was confirmed that the base-discriminating ability was increased by 4.8° C.

Example 9

2-N-((Dimethylamino)methylene)-5'-O-(4,4'-dimethoxytrityl)-6-O-diphenylcarbamoyl-2'-O-methyl-3-deazaguanosine (290 mg, 0.342 mmol) was dissolved in 28% aqueous ammonia: 40% methylamine/methanol solution: pyridine (2:2:1, v/v/v) (3.5 mL) at 55° C. The resulting mixture was stirred for 5 hours and then extracted with chloroform (100 mL)/5% brine (70 mL) twice. The organic layer was evaporated under reduced pressure, and the residue was purified by silica gel column chromatography (N60: spherical neutral silica gel) with methanol/4% chloroform containing 1% triethylamine to give 5'-O-(4,4'-dimethoxytrityl)-2'-O-methyl-3-deazaguanosine (150 mg, 73%).

$^1$H NMR (DMSO-d6) σ 3.39 (3H, s), 3.72 (6H, s), 4.01 (1H, d, J=3.4 Hz), 4.14 (1H, t, J=4.9 Hz), 4.21 (1H, t, J=5.6 Hz), 5.27 (1H, d, J=6.4 Hz), 5.45 (1H, s), 5.56 (2H, d, J=8.3 Hz), 5.66 (1H, d, J=4.6 Hz), 6.82-6.84 (4H, m) 7.18-7.32 (9H, m), 7.77 (1H, s), 10.32 (1H, sbr): MS m/z calcd for $C_{33}H_{35}N_4O_7^+$: 599.2506. found 599.2550.

Then, the given 5'-O-(4,4'-dimethoxytrityl)-2'-O-methyl-3-deazaguanosine (170 mg, 0.284 mmol) was azeotroped with anhydrous pyridine three times and then dissolved in anhydrous acetonitrile (2.8 mL), and hexamethyldisilazane was added thereto at room temperature. The mixture was stirred for 2 hours. The solvent was evaporated under reduced pressure. The residue was dissolved in anhydrous pyridine (2.8 mL), and acetyl chloride (44 μL, 0.65 mmol) was added thereto at 0° C. Then, the reaction solution was returned to room temperature and stirred for 3 hours. Then, the reaction was terminated by adding water thereto. After the addition of aqueous ammonia, the mixture was stirred overnight and then extracted with ethyl acetate (100 mL)/brine (70 mL) twice. The organic layer was dried over anhydrous magnesium sulfate, and the solvent was evaporated under reduced pressure. The residue was purified by silica gel column chromatography (N60: spherical neutral silica gel) with methanol/2% to 4% chloroform containing 1% triethylamine to give 2-N-acetyl-5'-O-(4,4'-dimethoxytrityl)-2'-O-methyl-3-deazaguanosine (120 mg, 65%).

$^1$H NMR (DMSO-d6) σ 2.09 (3H, s), 3.14-3.20 (2H, m), 3.41 (3H, s), 3.71 (6H, s), 4.06 (1H, dd, J=5.1 Hz, J=8.6 Hz), 4.20 (1H, t, J=4.7 Hz), 4.24 (1H, dd, J=5.4 Hz, J=11.5 Hz), 5.31 (1H, d, J=6.4 Hz), 5.86 (1H, d, J=4.4 Hz), 6.45 (1H, sbr), 6.80-6.83 (4H, m), 7.15-7.29 (9H, m), 8.07 (1H, s), 10.54 (1H, sbr), 11.28 (1H, sbr): MS m/z calcd for $C_{35}H_{37}N_4O_8^+$: 641.2611. found 641.2642.

The above-obtained 2-N-acetyl-5'-O-(4,4'-dimethoxytrityl)-2'-O-methyl-3-deazaguanosine (119 mg, 0.185 mmol) was azeotroped with anhydrous toluene three times and then dissolved in anhydrous methylene chloride (1.9 mL), and diisopropylethylamine (54 μL, 0.27 mmol) and then chloro(2-cyanoethoxy)-(N,N'-diisopropylamino)phosphine (57 μL, 0.259 mmol) were added thereto. The mixture was stirred at room temperature for 4.5 hours. Then, the reaction was terminated by adding water thereto. The reaction solution was extracted with methylene chloride (40 mL)/5% sodium bicarbonate water (50 mL) five times. The organic layer was dried over anhydrous sodium sulfate, and the solvent was evaporated under reduced pressure. The residue was purified by gel filtration chromatography (acetonitrile) to give 2-N-acetyl-5'-O-(4,4'-dimethoxytrityl)-2'-O-methyl-3-deazaguanosine-3'-(2-cyanoethyl-N,N-diisopropylphosphoroamidite, 47 mg, 30%).

$^1$H NMR (CDCl$_3$-d1) σ 1.03-1.05 (4H, m), 1.17-1.29 (8H, m), 2.02 (3H, m), 2.37, 2.68 (2H, m), 3.36-3.67 (7H, m), 3.77 (6H, m), 3.87-3.98 (1H, m), 4.13-4.16 (1H, m), 4.32-4.38 (1H, m), 4.47-4.50 (1H, m), 5.85 (1H, m), 6.80 (4H, m), 7.20-7.49 (9H, m), 7.96 (1H, m), 10.21 (1H, sbr), 11.80 (1H, sbr): $^{31}$P NMR (CDCl$_3$-d1) σ 151.6, 152.2.

Example 10

3',5'-Bis-O-(tert-butyldimethylsilyl)deoxyguanosine (1.5 g, 3.02 mmol) was azeotroped with anhydrous pyridine three times and then dissolved in anhydrous pyridine (15 mL), and trimethylsilyl chloride (576 μL, 4.53 mmol) was added thereto. The mixture was stirred at room temperature for 1 hour, and then phenyl chloroformate (569 μL, 3.93 mmol) was added thereto. The mixture was stirred at room temperature for 4 hours. A 40% methylamine methanol solution (1.8 mL, 15.1 mmol) was added thereto, and the mixture was stirred at room temperature for 2 hours. The reaction solution was extracted with ethyl acetate (200 mL)/water (150 mL) once and then with ethyl acetate (200 mL)/brine (150 mL) twice. The organic layer was dried over anhydrous magnesium sulfate, and the solvent was evaporated under reduced pressure. The residue was purified by NH silica gel column chromatography with methanol/50% to 80% chloroform to give 3',5'-bis-O-(tert-butyldimethylsilyl)-2-N-methylcarbamoyldeoxyguanosine (1.38 g, 78%).

$^1$H NMR (DMSO-d6) δ 0.01 (6H, d), 0.08 (6H, s), 0.84 (9H, s), 0.86 (9H, s), 2.26-2.30 (1H, m), 2.61-2.67 (1H, m), 2.70 (3H, d, J=3.9 Hz), 3.62-3.71 (2H, m), 3.81 (1H, m), 4.48 (1H, m), 6.15 (1H, t, J=6.5 Hz), 7.02 (1H, sbr), 8.05 (1H, s), 10.26 (1H, sbr), 11.98 (1H, sbr): $^{13}$C NMR (DMSO-d6) δ −5.6, −5.6, −5.0, −4.9, 17.6, 17.9, 25.6, 25.7, 26.1, 62.6, 71.9, 82.5, 87.1, 119.1, 136.2, 148.9, 149.2, 155.5: MS m/z calcd for $C_{24}H_{44}N_6O_5Si_2^+$: 553.2990. found 553.3027.

The above-obtained 3',5'-bis-O-(tert-butyldimethylsilyl)-2-N-methylcarbamoyldeoxyguanosine (889 mg, 1.61 mmol) was azeotroped with anhydrous pyridine three times and then dissolved in anhydrous pyridine (16 mL), and diisopropylethylamine (421 μL, 2.41 mmol) and then diphenylcarbamoyl chloride (424 mg, 1.93 mmol) were added thereto. The mixture was stirred at room temperature for 0.5 hours. Then, after addition of ethyl acetate (10 mL), the reaction was terminated by adding sodium bicarbonate water (10 mL) thereto. The reaction solution was extracted with ethyl acetate (150 mL)/sodium bicarbonate water (150 mL) once and then with ethyl acetate (150 mL)/brine (100 mL) twice. The organic layer was dried over anhydrous magnesium sulfate, and the solvent was evaporated under reduced pressure. The residue was purified by silica gel column chromatography (C200) with ethyl acetate/40% to 50% hexane to give 3',5'-bis-O-(tert-butyldimethylsilyl)-6-O-diphenylcarbamoyl-2-N-methylcarbamoyldeoxyguanosine (1.13 g, 94%).

$^1$H NMR (DMSO-d6) δ 0.00 (6H, s), 0.10 (6H, s), 0.83 (9H, s), 0.88 (9H, s), 2.34-2.39 (1H, m), 2.77 (3H, d, J=4.6 Hz), 2.79-2.84 (1H, m), 3.65-3.76 (2H, m), 3.86 (1H, m), 4.55 (1H, m), 6.39 (1H, t, J=6.5 Hz), 7.29-7.50 (10H, m), 8.36 (1H, dd, J=4.6 Hz, J=9.2 Hz), 8.49 (1H, s), 9.87 (1H, sbr): $^{13}$C NMR (DMSO-d6) δ −5.5, −4.9, −4.7, 17.6, 17.9, 25.6, 25.7, 26.3, 62.5, 71.7, 83.3, 87.3, 118.6, 127.4, 129.4, 141.6, 142.8, 153.4, 154.0, 154.0, 155.2: MS m/z calcd for $C_{37}H_{54}N_7O_6Si_2^+$: 748.3674. found 748.3677.

The above-obtained 3',5'-bis-O-(tert-butyldimethylsilyl)-6-O-diphenylcarbamoyl-2-N-methylcarbamoyldeoxyguanosine (1.13 g, 52 mmol) was azeotroped with anhydrous tetrahydrofuran three times and then dissolved in anhydrous tetrahydrofuran (15 mL), and triethylamine 3 hydrogen fluoride (743 μL, 4.56 mmol) was added thereto. The mixture was stirred at room temperature overnight. Then, after addition of toluene (5 mL), the solvent was evaporated under reduced pressure. The residue was purified by silica gel column chromatography (C200) with methanol/5% to 6% chloroform, and then ethyl acetate (5 mL) and diethyl ether (15 mL) were added thereto for precipitation. Then, the precipitate was purified by filtration to give 6-O-diphenylcarbamoyl-2-N-methylcarbamoyldeoxyguanosine (643 mg, 81%).

$^1$H NMR (DMSO-d6) δ 2.33-2.36 (1H, m), 2.67 (1H, m), 2.79 (3H, d, J=3.4 Hz), 3.50-3.60 (2H, m), 3.85 (1H, d, J=2.7 Hz), 4.41 (1H, s), 4.93 (1H, s), 5.34 (1H, d, J=3.2 Hz), 6.39 (1H, t, J=6.0 Hz), 7.31-7.48 (10H, m), 8.39 (1H, d, J=3.4 Hz), 8.56 (1H, s), 9.87 (1H, sbr): $^{13}$C NMR (DMSO-d6) δ 26.4, 61.3, 70.3, 83.4, 87.8, 118.7, 127.4, 129.4, 141.6, 143.2, 150.0, 153.4, 154.0, 154.1, 155.1: MS m/z calcd for $C_{25}H_{25}N_7O_6^+$: 520.1945. found 520.1945.

The thus obtained 6-O-diphenylcarbamoyl-2-N-methylcarbamoyldeoxyguanosine (643 mg, 1.24 mmol) was azeotroped with anhydrous pyridine three times and then dissolved in anhydrous pyridine (21 mL), and 4,4'-dimethoxytrityl chloride (629 mg, 1.86 mmol) was added thereto. The mixture was stirred at room temperature for 3 hours. Then, the reaction was terminated by adding sodium bicarbonate water (5 mL) thereto. The reaction solution was extracted with ethyl acetate (100 mL)/sodium bicarbonate water (100 mL) once and then with ethyl acetate (100 mL)/brine (80 mL) twice. The organic layer was dried over anhydrous magnesium sulfate, and the solvent was evaporated under reduced pressure. The residue was purified by silica gel column chromatography (N60: spherical neutral silica gel) with ethyl acetate/50% to 60% hexane containing 1% triethylamine to give 5'-O-(4,4'-dimethoxytrityl)-6-O-diphenylcarbamoyl-2-N-methylcarbamoyldeoxyguanosine (889 mg, 87%).

$^1$H NMR (DMSO-d6) σ 2.37-2.42 (1H, m), 2.76 (3H, d, J=4.6 Hz), 2.80-2.84 (1H, m), 3.12-3.19 (2H, m), 3.65 (6H, d, J=8.5 Hz), 3.96 (1H, d, J=2.4 Hz), 4.43 (1H, s), 5.36 (1H, d, J=3.7 Hz), 6.43 (1H, t, J=6.0 Hz), 6.73-6.78 (4H, m), 7.08-7.49 (19H, m), 8.42 (1H, d, J=4.6 Hz), 8.46 (1H, s), 9.88 (1H, s): $^{13}$C NMR (DMSO-d6) δ 26.4, 64.0, 70.2, 83.5, 85.4, 85.9, 113.0, 113.0, 118.9, 126.5, 127.6, 127.6, 129.4, 129.6, 129.7, 135.4, 135.6, 141.6, 143.2, 144.9, 149.9, 153.4, 153.9, 154.1, 155.2, 158.0: MS m/z calcd for $C_{46}H_{43}N_7NaO_8^+$: 844.3071. found 844.3075.

The given 5'-O-(4,4'-dimethoxytrityl)-6-O-diphenylcarbamoyl-2-N-methylcarbamoyldeoxyguanosine (760 mg, 0.925 mmol) was azeotroped with anhydrous toluene three times and anhydrous acetonitrile three times, and then dissolved in anhydrous methylene chloride (9.2 mL). To the resulting mixture, diisopropylethylamine (410 μL, 2.35 mmol) and then chloro(2-cyanoethoxy)-(N,N'-diisopropylamino)phosphine (410 μL, 1.85 mmol) were added. The mixture was stirred at room temperature for 2 hours. Then, the reaction was terminated by adding water (1 mL) thereto. The reaction solution was extracted with ethyl acetate (150 mL)/5% sodium bicarbonate water (100 mL) five times. The organic layer was dried over anhydrous sodium sulfate, and the solvent was evaporated under reduced pressure. The residue was purified by gel filtration chromatography (acetonitrile) to give a compound represented by Formula (22), 5'-O-(4,4'-dimethoxytrityl)-6-O-diphenylcarbamoyl-2-N-methylcarbamoyldeoxyguanosine-3'-(2-cyanoethyl-N,N-diisopropylphosphoroamidite (644 mg, 68%).

$^1$H NMR (CDCl$_3$-d1) δ 1.13-1.27 (14H, m), 2.43 (1H, m), 2.58-2.76 (3H, m), 2.94 (3H, m), 3.35 (2H, m), 3.61-3.84 (4H, m), 3.73 (6H, m), 4.29-4.33 (1H, m), 4.71 (1H, m), 6.35 (1H, m), 6.80 (4H, m), 7.18-7.43 (19H, m), 7.63 (1H, m), 8.09 (1H, m), 8.61 (1H, s): $^{13}$C NMR (CDCl$_3$-d1) σ 20.1, 20.2, 20.3, 20.4, 24.5, 24.5, 24.6, 26.7, 39.5, 39.7, 43.2, 43.3, 55.1, 55.1, 58.1, 58.1, 58.2, 58.3, 63.3, 63.4, 73.4, 73.6, 74.0, 74.1, 84.4, 85.7, 85.8, 86.0, 86.5, 113.1, 117.4, 117.5, 119.8, 126.9, 126.9, 127.8, 128.0, 128.0, 129.2, 129.9, 130.0, 130.0, 135.4, 135.5, 141.7, 144.4, 150.1, 153.0, 154.4, 154.5, 155.6, 155.6, 158.5: $^{31}$P NMR (CDCl$_3$-d1) σ 150.0, 150.3: MS m/z calcd for $C_{55}H_{60}N_9NaO_9P^+$: 1044.4149. found 1044.3683.

[Formula 37]

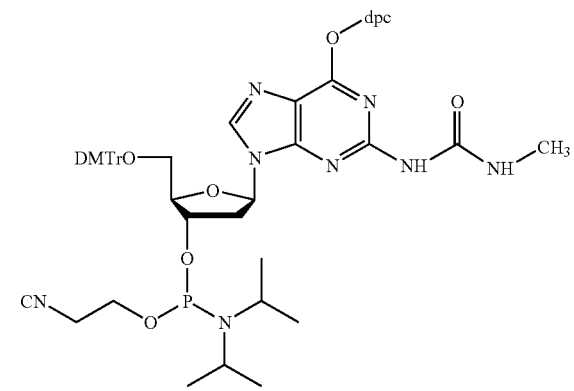

(22)

Example 11

3',5'-Bis-O-(tert-butyldimethylsilyl)deoxyguanosine (2.8 g, 5.83 mmol) was azeotroped with anhydrous pyridine three times and then dissolved in anhydrous pyridine (60 mL), and trimethylsilyl chloride (1.11 mL, 8.75 mmol) was added thereto. The mixture was stirred at room temperature for 1 hour, and then phenyl chloroformate (1.10 mL, 8.75 mmol) was added thereto. The resulting mixture was stirred at room temperature for 4 hours, and 28% aqueous ammonia (4.1 mL, 29.1 mmol) was added thereto. The resulting mixture was stirred at room temperature for 2 hours. The reaction solution was extracted with ethyl acetate (250 mL)/water (200 mL) once and then with ethyl acetate (250 mL)/brine (150 mL) twice. The organic layer was dried over anhydrous magnesium sulfate, and the solvent was evaporated under reduced pressure. The residue was purified by NH silica gel column chromatography (25 g) with methanol/6% to 30% chloroform to give 3',5'-bis-O-(tert-butyldimethylsilyl)-2-N-carbamoyldeoxyguanosine (2.12 g, 68%).

$^1$H NMR (DMSO-d6) δ 0.02 (6H, d), 0.10 (6H, s), 0.86 (9H, s), 0.88 (9H, s), 2.26-2.35 (1H, m), 2.62-2.68 (1H, m), 3.62-3.71 (2H, m), 3.82 (1H, m), 4.48 (1H, m), 6.15 (1H, t, J=6.8 Hz), 6.41 (1H, sbr), 7.23 (1H, sbr), 8.07 (1H, s), 10.07 (1H, sbr), 12.03 (1H, sbr): $^{13}$C NMR (DMSO-d6) δ−5.5, −5.5, −5.0, −4.8, 17.7, 18.0, 25.7, 25.8, 62.6, 71.9, 82.6, 87.1, 119.2, 136.4, 148.9, 1491, 156.2: MS m/z calcd for $C_{23}H_{43}N_6O_5Si_2^+$: 539.2834. found 539.2809.

The above-obtained 3',5'-bis-O-(tert-butyldimethylsilyl)-2-N-carbamoyldeoxyguanosine (1.23 g, 2.29 mmol) was azeotroped with anhydrous pyridine three times and then dissolved in anhydrous pyridine (23 mL). To the resulting solution, diisopropylethylamine (797 μL, 4.58 mmol) and then diphenylcarbamoyl chloride (689 mg, 2.98 mmol) were added, and the mixture was stirred at room temperature for 0.5 hours. Then, the reaction was terminated by adding sodium bicarbonate water (5 ml) thereto. The reaction solution was extracted with ethyl acetate (180 mL)/sodium bicarbonate water (150 mL) once and then with ethyl acetate (180 mL)/brine (100 mL) twice. The organic layer was dried over anhydrous magnesium sulfate, and the solvent was evaporated under reduced pressure. The residue was purified by silica gel column chromatography (C200) with ethyl acetate/50% to 60% hexane to give 3',5'-bis-O-(tert-butyldimethylsilyl)-2-N-carbamoyl-6-O-diphenylcarbamoyldeoxyguanosine (1.53 g, 91%).

$^1$H NMR (DMSO-d6) δ 0.00 (6H, s), 0.10 (6H, s), 0.82 (9H, s), 0.88 (9H, s), 2.33-2.35 (1H, m), 2.62-2.67 (1H, m), 3.65-3.74 (2H, m), 3.84 (1H, m), 4.55 (1H, m), 6.34 (1H, t, J=6.5 Hz), 7.05 (1H, sbr) 7.11-7.48 (10H, m), 8.36 (1H, dd, J=4.6 Hz, J=9.2 Hz), 7.98 (1H, sbr), 8.49 (1H, s), 9.71 (1H, s): $^{13}$C NMR (DMSO-d6) δ −5.5, −5.5, −5.0, −4.7, 17.7, 18.0, 25.7, 25.8, 62.5, 71.6, 83.2, 87.3, 118.6, 127.3, 129.4, 141.6, 142.8, 149.9, 153.4, 154.2, 154.3, 155.1: MS m/z calcd for $C_{36}H_{52}N_7O_6Si_2^+$: 734.3518. found 734.3581.

The above-obtained 3',5'-bis-O-(tert-butyldimethylsilyl)-2-N-carbamoyl-6-O-diphenylcarbamoyldeoxyguanosine (1.53 g, 2.09 mmol) was azeotroped with anhydrous tetrahydrofuran three times and dissolved in anhydrous tetrahydrofuran (10 mL), and triethylamine 3 hydrogen fluoride (1.02 mL, 6.27 mmol) was added thereto. The mixture was stirred at room temperature overnight, and then toluene (10 mL) was added thereto. The solvent was evaporated under reduced pressure, and the residue was purified by silica gel column chromatography (N60: spherical neutral silica gel) with methanol/4% to 10% chloroform to give 2-N-carbamoyl-6-O-diphenylcarbamoyldeoxyguanosine (1.21 g, quant).

$^1$H NMR (DMSO-d6) δ 2.31-2.35 (1H, m), 2.65-2.70 (1H, m), 3.49-3.58 (2H, m), 3.85 (1H, dd, J=4.5 Hz, J=7.6 Hz), 4.44 (1H, dd, J=3.2 Hz, J=5.4 Hz), 4.92 (1H, s), 5.33 (1H, d, J=3.9 Hz), 6.35 (1H, t, J=6.7 Hz), 7.12 (1H, sbr) 7.29-7.48 (10H, m), 8.06 (1H, sbr), 8.57 (1H, s), 9.75 (1H, s): $^{13}$C NMR (DMSO-d6) δ 61.4, 70.5, 83.4, 88.0, 118.7, 127.4, 129.4, 141.6, 143.2, 150.0, 153.4, 154.2, 154.3, 155.2: MS m/z calcd for $C_{24}H_{24}N_7O_6^+$: 506.1788. found 506.1796.

The above-obtained 2-N-carbamoyl-6-O-diphenylcarbamoyldeoxyguanosine (1.19 g, 2.35 mmol) was azeotroped with anhydrous pyridine three times and dissolved in anhydrous pyridine (23 mL), and 4,4'-dimethoxytrityl chloride (917 mg, 2.70 mmol) was added thereto. The mixture was stirred at room temperature for 2 hours, and sodium bicarbonate water (8 mL) was added thereto to terminate the reaction. Then, the reaction solution was extracted with ethyl acetate (150 mL)/sodium bicarbonate water (120 mL) once and then with ethyl acetate (150 mL)/brine (100 mL) twice. The organic layer was dried over anhydrous magnesium sulfate, and the solvent was evaporated under reduced pressure. The residue was purified by silica gel column chromatography (N60: spherical neutral silica gel) with methanol/2% to 3% chloroform containing 1% triethylamine to give 2-N-carbamoyl-5'-O-(4,4'-dimethoxytrityl)-6-O-diphenylcarbamoyldeoxyguanosine (1.45 g, 76%).

$^1$H NMR (DMSO-d6) δ 2.35-2.40 (1H, m), 2.78-2.83 (1H, m), 3.11-3.16 (2H, m), 3.65 (6H, d, J=7.8 Hz), 3.95 (1H, dd, J=4.4 Hz, J=9.5 Hz), 4.43 (1H, m), 5.35 (1H, d, J=4.9 Hz), 6.39 (1H, t, J=6.1 Hz), 6.73-6.79 (4H, m), 7.09-7.48 (19H, m), 7.48 (1H, sbr), 8.46 (1H, s), 9.73 (1H, s): $^{13}$C NMR (DMSO-d6) δ 54.9, 54.9, 63.9, 70.2, 79.2, 83.4, 85.4, 86.0, 113.0, 113.0, 118.8, 126.5, 127.6, 127.6, 129.4, 129.6, 129.7, 135.4, 135.6, 141.6, 143.0, 144.9, 149.6, 153.5, 154.2, 154.3, 155.2, 158.0: MS m/z calcd for $C_{45}H_{41}N_7NaO_8^+$: 830.2914. found 830.2907.

The above-obtained 2-N-carbamoyl-5'-O-(4,4'-dimethoxytrityl)-6-O-diphenylcarbamoyldeoxyguanosine (250 mg, 0.309 mmol) was azeotroped with anhydrous toluene three times and with anhydrous acetonitrile three times and then dissolved in anhydrous methylene chloride (3.0 mL). To the resulting solution, diisopropylethylamine (27 μL, 0.145 mmol), 1H-tetrazole (11 mg, 0.145 mmol), and then (2-cyanoethoxy)-di-(N,N'-diisopropylamino)phosphine (410 μL, 1.85 mmol) were added. The resulting mixture was stirred at room temperature for 2 hours. The reaction solution was extracted with ethyl acetate (50 mL)/0.2 M sodium hydroxide aqueous solution (40 mL) five times. Then, the organic layer was dried over anhydrous sodium sulfate, and the solvent was evaporated under reduced pressure. The residue was purified by gel filtration chromatography (acetonitrile) and extracted with ethyl acetate (50 mL)/0.2 M sodium hydroxide aqueous solution (70 mL) five times to give a compound represented by the following Formula (23), 2-N-carbamoyl-5'-O-(4,4'-dimethoxytrityl))-6-O-diphenylcarbamoyldeoxyguanosine-3'-(2-cyanoethyl-N,N-diisopropylphosphoroamidite, 245 mg, 75%).

$^1$H NMR (CDCl$_3$-d1) δ 1.11-1.33 (14H, m), 2.46 (1H, m), 2.55-2.74 (3H, m), 3.32-3.40 (2H, m), 3.57-3.87 (4H, m), 3.75 (6H, m), 4.26-4.32 (1H, m), 4.67-4.72 (1H, m), 5.36 (1H, sbr), 6.35 (1H, m), 6.79 (4H, m), 7.17-7.50 (19H, m), 8.07 (1H, m), 8.53 (1H, sbr): $^{13}$C NMR (CDCl$_3$-d1) δ 20.6, 20.7, 20.8, 20.9, 24.9, 25.0, 25.0, 40.2, 43.6, 43.6, 43.7, 43.7, 55.6, 55.6, 58.5, 58.6, 58.6, 58.7, 63.7, 63.8, 73.9, 74.0, 74.4, 74.5, 84.7, 84.8, 86.2, 86.2, 86.4, 86.9, 113.6, 117.8, 117.9, 120.5, 127.3, 127.4, 128.3, 128.4, 128.5, 129.6, 130.3, 130.4, 130.4, 135.8, 135.8, 135.9, 135.9, 142.1, 144.7, 150.4, 153.1, 154.8, 154.9, 155.0, 156.2, 159.0: $^{31}$P NMR (CDCl$_3$-d1) σ 149.9: MS m/z calcd for $C_{54}H_{59}N_9NaO_9P^+$: 1030.3993. found 1033.4001.

[Formula 38]

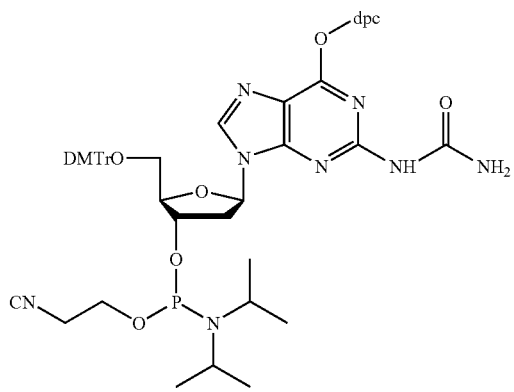

(23)

Example 12

3',5'-Bis-O-(tert-butyldimethylsilyl)deoxyguanosine (3.0 g, 6.05 mmol) was azeotroped with anhydrous toluene three times and then dissolved in anhydrous dimethylformamide (30 mL), and then sodium hydride (199 mg, 7.86 mmol) was added thereto. The mixture was stirred at 70° C. for 1 hour. Then, the reaction solution was returned to room temperature, and methyl thioisocyanate (1.24 mL, 18.2 mmol) was added thereto. The mixture was stirred at 70° C. for 36 hours. The reaction solution was poured into a 0.5 M ammonium acetate buffer solution (150 mL), and the resulting mixture was extracted with ethyl acetate (200 mL)/0.5 M ammonium acetate buffer solution (150 mL) once and then with ethyl acetate (200 mL)/water (150 mL) twice. The organic layer was evaporated under reduced pressure, and the residue was subjected to NH silica gel column chromatography to remove raw materials with methanol/5% chloroform. The gel was collected and eluted with methanol/80% chloroform 40 times. The eluate was concentrated to give 3',5'-bis-O-(tert-butyldimethylsilyl)-2-N-methylthiocarbamoyldeoxyguanosine (1.65 g, 48%).

$^1$H NMR (DMSO-d6) δ 0.01 (6H, d), 0.09 (6H, s), 0.84 (9H, s), 0.87 (9H, s), 2.30-2.34 (1H, m), 2.58-2.63 (1H, m), 3.07 (3H, s), 3.63-3.74 (2H, m), 3.83 (1H, dd, J=4.4 Hz, J=8.5 Hz), 4.51 (1H, m), 6.30 (1H, t, J=6.5 Hz), 8.06 (1H, s), 10.73 (2H, sbr), 11.98 (1H, sbr): $^{13}$C NMR (DMSO-d6) δ −5.6, −5.5, −5.0, −4.8, 17.6, 17.9, 25.6, 25.7, 25.7, 31.7, 62.4, 71.5, 82.7, 86.9, 119.8, 136.6, 147.4, 179.0: MS m/z calcd for $C_{24}H_{44}N_6O_4SSi_2^+$: 569.2762. found 569.2750.

The above-obtained 3',5'-bis-O-(tert-butyldimethylsilyl)-2-N-methylthiocarbamoyldeoxyguanosine (1.0 g, 1.76 mmol) was azeotroped with anhydrous pyridine three times and dissolved in anhydrous pyridine (17 mL). To the resulting solution, diisopropylethylamine (511 μL, 3.16 mmol) and then diphenylcarbamoyl chloride (489 mg, 2.11 mmol) were added. The mixture was stirred at room temperature for 0.5 hours, and then sodium bicarbonate water (5 mL) was added thereto to terminate the reaction. Then, the reaction solution was extracted with ethyl acetate (150 mL)/sodium bicarbonate water (120 mL) once and then with ethyl acetate (150 mL)/brine (100 mL) twice. The organic layer was dried over anhydrous magnesium sulfate, and the solvent was evaporated under reduced pressure. The residue was purified by silica gel column chromatography (N60: spherical neutral silica gel) with ethyl acetate/40% to 50% hexane to give 3',5'-bis-O-(tert-butyldimethylsilyl)-6-O-diphenylcarbamoyl-2-N-methylthiocarbamoyldeoxyguanosine (1.09 g, 81%).

$^1$H NMR (DMSO-d6) δ 0.00 (6H, s), 0.11 (6H, s), 0.82 (9H, s), 0.89 (9H, s), 2.34-2.39 (1H, m), 2.81-2.87 (1H, m), 3.11 (3H, d, J=4.6 Hz), 3.65-3.78 (2H, m), 3.86 (1H, dd, J=4.5 Hz, J=8.8 Hz), 4.55 (1H, m), 6.42 (1H, t, J=6.4 Hz), 7.29-7.50 (10H, m), 8.56 (1H, s), 10.59 (1H, dd, J=4.5 Hz, J=9.1 Hz), 10.78 (1H, s): $^{13}$C NMR (DMSO-d6) δ −5.5, −5.5, −5.0, −4.8, 17.7, 17.9, 25.6, 25.7, 31.9, 62.4, 71.6, 83.6, 87.3, 119.1, 127.3, 129.4, 141.5, 143.5, 149.7, 15.0, 153.6, 155.0, 179.7: MS m/z calcd for $C_{37}H_{54}N_7O_5SSi_2^+$: 764.3446. found 764.3432.

The above-obtained 3',5'-bis-O-(tert-butyldimethylsilyl)-6-O-diphenylcarbamoyl-2-N-methylthiocarbamoyldeoxyguanosine (900 mg, 1.17 mmol) was azeotroped with anhydrous tetrahydrofuran three times and dissolved in anhydrous tetrahydrofuran (6.0 mL), and triethylamine 3 hydrogen fluoride (574 μL, 3.51 mmol) was added thereto. The mixture was stirred at room temperature overnight, and then toluene (5 mL) was added thereto. The solvent was evaporated under reduced pressure. To the residue, methanol (5 mL) and hexane (25 mL) were added for precipitation. The resulting precipitate was purified by filtration to give 6-O-diphenylcarbamoyl-2-N-methylthiocarbamoyldeoxyguanosine (504 mg, 80%).

$^1$H NMR (DMSO-d6) δ 2.32-2.37 (1H, m), 2.70-2.75 (1H, m), 3.12 (3H, d, J=4.4 Hz), 3.48-3.61 (2H, m), 3.85 (1H, dd, J=4.2 Hz, J=8.1 Hz), 4.42 (1H, dd, J=3.8 Hz, J=5.9 Hz), 4.92 (1H, t, J=5.4 Hz), 5.34 (1H, d, J=4.2 Hz), 6.41 (1H, t, J=6.5 Hz), 7.30-7.50 (10H, m), 8.62 (1H, s), 10.56 (1H, dd, J=4.4 Hz, J=9.1 Hz), 10.80 (1H, s): $^{13}$C NMR (DMSO-d6) δ 32.1, 61.2, 70.2, 83.8, 87.8, 119.3, 127.3, 129.4, 141.5, 144.0, 149.8, 152.0, 153.6, 155.0, 179.7: MS m/z calcd for $C_{25}H_{26}N_7O_5S^+$: 536.1716. found 536.1546.

The above-obtained 6-O-diphenylcarbamoyl-2-N-methylthiocarbamoyldeoxyguanosine (400 mg, 0.744 mmol) was azeotroped with anhydrous pyridine three times and dissolved in anhydrous pyridine (8.0 mL), and 4,4'-dimethoxytrityl chloride (278 mg, 0.818 mmol) was added thereto. The mixture was stirred at room temperature for 3 hours, and then sodium bicarbonate water (3 mL) was added thereto to terminate the reaction. The reaction solution was extracted with ethyl acetate (150 mL)/sodium bicarbonate water (120 mL) once and with ethyl acetate (150 mL)/brine (100 mL) twice. Then, the organic layer was dried over anhydrous magnesium sulfate. The solvent was evaporated under reduced pressure, and the residue was purified by silica gel column chromatography (N60: spherical neutral silica gel) with methanol/3% to 4% chloroform containing 1% triethylamine to give 5'-O-(4, 4'-dimethoxytrityl)-6-O-diphenylcarbamoyl-2-N-methylthiocarbamoyldeoxyguanosine (570 mg, 78%).

$^1$H NMR (DMSO-d6) δ 2.37-2.42 (1H, m), 2.84-2.89 (1H, m), 3.01 (3H, d, J=4.4 Hz), 3.11-3.21 (2H, m), 3.65 (6H, d, J=10.2 Hz), 3.97 (1H, m), 4.46 (1H, t, J=5.5 Hz), 5.35 (1H, d, J=4.6 Hz), 6.45 (1H, t, J=5.4 Hz), 6.72-6.77 (4H, m), 7.06-7.50 (19H, m), 8.53 (1H, s), 10.62 56 (1H, dd, J=4.4 Hz, J=8.8 Hz), 10.82 (1H, s): $^{13}$C NMR (DMSO-d6) δ 32.0, 40.0, 54.9, 55.0, 64.0, 70.2, 84.0, 85.3, 86.1, 113.0, 113.0, 119.5, 126.5, 127.6, 127.6, 129.4, 129.6, 129.7, 135.3, 135.7, 141.6, 144.2, 144.9, 149.8, 152.0, 153.5, 155.0, 158.0, 179.8: MS m/z calcd for $C_{46}H_{43}N_7NaO_7S^+$: 860.2842. found 860.2859.

The above-obtained 5'-O-(4,4'-dimethoxytrityl)-6-O-diphenylcarbamoyl-2-N-methylthiocarbamoyldeoxyguanosine (250 mg, 0.298 mmol) was azeotroped with anhydrous toluene three times and with anhydrous acetonitrile three times and then dissolved in anhydrous methylene chloride (3.0 mL). To the resulting solution, diisopropylethylamine (83 μL, 0.477 mmol) and chloro(2-cyanoethoxy)-(N,N'-diisopropylamino)phosphine (86 μL, 0.387 mmol) were added. The mixture was stirred at room temperature for 2 hours, and then water (1 mL) was added thereto to terminate the reaction. The reaction solution was extracted with ethyl acetate (50 mL)/5% sodium bicarbonate water (50 mL) five times. The organic layer was dried over anhydrous sodium sulfate, and the solvent was evaporated under reduced pressure. The residue was purified by gel filtration chromatography (acetonitrile) and then extracted with ethyl acetate (50 mL)/0.2 M sodium hydroxide aqueous solution (50 mL) five times to give a compound represented by the following Formula (24), 5'-O-(4,4'-dimethoxytrityl))-6-O-diphenylcarbamoyl-2-N-methylthiocarbamoyldeoxyguanosine-3'-(2-cyanoethyl-N, N-diisopropylphosphoroamidite, 144 mg, 47%).

$^1$H NMR (CDCl$_3$-d1) δ 1.12-1.29 (14H, m), 2.46 (1H, m), 2.57-2.75 (3H, m), 2.25 (3H, m), 3.30-3.38 (2H, m), 3.58-3.88 (4H, m), 3.75 (6H, m), 4.27-4.33 (1H, m), 4.67 (1H, m), 6.32 (1H, m), 6.79 (4H, m), 7.16-7.43 (19H, m), 8.10 (1H, m), 8.52 (1H, s), 10.59 (1H, m): $^{13}$C NMR (CDCl$_3$-d1) 520.3, 20.4, 20.6, 20.6, 24.7, 24.7, 24.8, 32.6, 39.8, 43.4, 43.4, 43.5, 55.3, 58u.2, 58.3, 58.4, 58.4, 63.4, 63.6, 73.6, 74.1, 74.2, 84.8, 84.8, 86.1, 86.1, 86.3, 86.7, 113.3, 113.3, 117.5, 117.6, 120.2, 120.3, 127.1, 127.1, 128.0, 128.2, 128.2, 129.4, 130.1, 130.1, 130.2, 135.5, 135.6, 135.7, 141.7, 142.4, 144.5, 150.0, 151.8, 158.7, 158.7, 180.0: $^{31}$P NMR (CDCl$_3$-d1) σ 150.0, 150.2: MS m/z calcd for $C_{55}H_{60}N_9NaO_8PS^+$: 1060.3921. found 1060.3889.

[Formula 39]

(24)

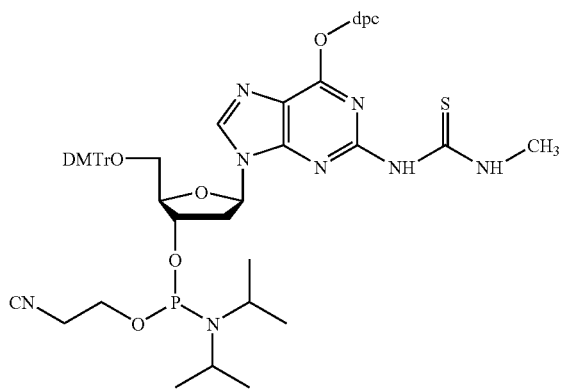

Example 13

2'-O-Me-5'-(CGGCXGAGGAG) (SEQ ID NO: 9, X=2'-O-methyl-2-N-acetyl-3-deazaguanosine), which is 2'-O-methyl RNA, was synthesized using 2'-O-methyl-3'-O-(2-cyanoethoxy group ethyl-N,N'-diisopropylphosphoroamidite)-5'-O-(4,4'-dimethoxytrityl)-2-N-acetyl-3-deazaguanosine prepared in Example 3. The synthesis was conducted using DNA/RNA Synthesizer 392 of Applied Biosystem Inc. (ABI). The synthesis of 2'-O-methyl RNA oligomer by an autosynthesizer was conducted using a solid phase support (1 μmol) supporting 2'-O-methylguanine purchased from Glen Research. Nucleotide residues other than the nucleotide residue corresponding to X were synthesized according to a typical RNA synthesis protocol of the autosynthesizer, and the oligonucleotide residue at the X-position was manually synthesized by elongation according to the following protocol 1) to 3) and washing with acetonitrile between each step.

1) Coupling
Amidite unit (20 μmol), 1H-tetrazole (80 μmole), acetonitrile/methylene chloride (200 μL/50 μL): 5 minutes 2) Oxidation
0.1 M Iodine/pyridine-water (180 μL-20 μL): 2 minutes 3) 3% trichloroacetic acid/methylene chloride (1 mL)×3

After the completion of the reaction for strand elongation, the strand was cut out by aqueous ammonia using an autocleavage function of the autosynthesizer, and then aqueous ammonia/ethanol (1.5 mL/0.5 mL) was added thereto. The mixture was left at room temperature for 24 hours. The resulting solution was filtered through a C18 cartridge to remove impurities, and then a DMTr group was cleaved by 2% TFA water in the cartridge column. The target material was eluted with water containing 20% acetonitrile. The resulting solution was lyophilized and then subjected to purification by anion exchange HPLC.

MALDI-TOF mass: calcd. 3456.6. found 3456.7.

Melting temperatures (Tm) of double strands of the above-obtained oligonucleotide and its complementary RNA having a sequence of 5'-CUCCYCGCCG-3' (SEQ ID NO: 10, Y=adenosine, guanosine, cytidine, or uridine) or DNA having a sequence of 5'-CTCCYCGCCG-3' (SEQ ID NO: 11, Y=2'-deoxyadenosine, 2'-deoxyguanosine, 2'-deoxycytidine, or thymidine) were measured. The measurement was conducted by the same method as that in Example 6. As a control, an oligonucleotide having a base sequence represented by SEQ ID NO: 9 in which X is guanosine was investigated.

The measurement was conducted in a 10 mM sodium phosphate buffer solution (pH 7.0) containing 0.1 M NaCl and 0.1 mM EDTA using 2 μM of each oligonucleotide.

Table 5 shows the results (measurement result 1) of a test of RNA having a base sequence represented by SEQ ID NO: 10, and Table 6 shows the results (measurement result 2) of a test of DNA having a base sequence represented by SEQ ID NO: 11.

TABLE 5

| X | Y | Tm(° C.) | ΔTm(° C.) |
|---|---|---|---|
| G | C | 71 | — |
| G | A | 50 | −21 |
| G | G | 54 | −17 |
| G | U | 62 | −9 |
| ad3G | C | 70 | — |
| ad3G | A | 51 | −19 |
| ad3G | G | 57 | −13 |
| ad3G | U | 55 | −15 |

TABLE 6

| X | Y | Tm(° C.) | ΔTm(° C.) |
|---|---|---|---|
| G | C | 59 | — |
| G | A | 40 | −19 |
| G | G | 41 | −18 |
| G | T | 50 | −9 |
| ad3G | C | 60 | — |
| ad3G | A | 38 | −22 |
| ad3G | G | 43 | −18 |
| ad3G | T | 46 | −14 |

In the results of measurement result 1, the Tm of the oligonucleotide containing 2'-O-methyl-2-N-acetyl-3-deazaguanosine (ad3G) at the X position with the complementary strand (Y=C) was equivalent to that of the oligonucleotide containing 2'-O-methyl-guanosine (G) at the X position (70° C. and 71° C.).

On the other hand, in the case of the most stable mismatching, the Tm (57° C., Y=G) of the oligonucleotide containing ad3G at the X position was lower than that (62° C., Y=U) of the oligonucleotide containing G at the X position by 5° C. It is obvious by this result that an oligonucleotide containing ad3G is improved in the mismatching base-discriminating ability.

In the results of measurement result 2, the Tm of the oligonucleotide containing 2'-O-methyl-2-N-acetyl-3-deaza-guanosine (ad3G) at the X position with its complementary strand (Y=C) was equivalent to that of the oligonucleotide containing deoxyguanosine (G) at the X position (60° C. and 59° C.).

On the other hand, in the case of the most stable mismatching, the Tm (46° C., Y=T) of the oligonucleotide containing ad3G at the X position was lower than that (50° C., Y=T) of the oligonucleotide containing G at the X position by 4° C. It is obvious by this result that an oligonucleotide containing ad3G is improved in the mismatching base-discriminating ability.

Example 14

An oligonucleotide containing 2'-deoxy-2-N-carbamoylguanosine was synthesized using 2-N-carbamoyl-5'-O-(4, 4'-dimethoxytrityl))-6-O-diphenylcarbamoyldeoxyguanosine-3'-(2-cyanoethyl-N,N-diisopropylphosphoroamidite) (245 mg, 75%) prepared in Example 11. The synthesized DNA contains a sequence of 5'-CGGCXAGGAG-3' (SEQ ID NO: 12, X represents 2'-deoxy-2-N-carbamoylguanosine). The synthesis was conducted using DNA/RNA Synthesizer 392 of Applied Biosystem Inc. A natural-type phosphoroamidite unit and other necessary reagents were purchased from Glen Research Inc. A phosphoroamidite unit synthesized in raw material synthesis example (appendix 16) was dissolved in anhydrous acetonitrile (0.1 M) and applied to a DNA autosynthesizer. The deprotection of base was conducted by addition of aqueous ammonia (2 mL) and leaving it at room temperature for 12 hours. The subsequent purification was conducted as in Example 13.

MALDI-TOF mass: calcd. 3158.4. found 3158.6.

Example 15

An oligonucleotide containing 2'-deoxy-2-N-methylcarbamoylguanosine was synthesized using 5'-O-(4,4'-dimethoxytrityl)-6-O-diphenylcarbamoyl-2-N-methylcarbamoyldeoxyguanosine-3'-(2-cyanoethyl-N,N-diisopropylphosphoroamidite) prepared in Example 10. The synthesized DNA has a sequence of 5'-CGGCXAGGAG-3' (SEQ ID NO: 13, X represents 2'-deoxy-2-N-methylcarbamoylguanosine). The synthesis was conducted using DNA/RNA Synthesizer 392 of Applied Biosystem Inc. A natural-type phosphoroamidite unit and other necessary reagents were purchased from Glen Research Inc. The phosphoroamidite unit used was dissolved in anhydrous acetonitrile (0.1 M) and applied to a DNA autosynthesizer. The deprotection of the base was conducted by addition of aqueous ammonia (2 mL) and leaving it at room temperature for 12 hours. The subsequent purification was conducted as in Example 14.

MALDI-TOF mass: calcd. 3172.5 found 3172.6.

Example 16

An oligonucleotide containing 2'-deoxy-2-N-methylthiocarbamoylguanosine was synthesized using 5'-O-(4,4'-dimethoxytrityl)-6-O-diphenylcarbamoyl-2-N-methylthiocarbamoyldeoxyguanosine-3'-(2-cyanoethyl-N,N-diisopropylphosphoroamidite) prepared in Example 12. The synthesized DNA has a sequence of 5'-CGGCXAGGAG-3' (X represents 2'-deoxy-2-N-methylthiocarbamoylguanosine). The synthesis was conducted using DNA/RNA Synthesizer 392 of Applied Biosystem Inc. A natural-type phosphoroamidite unit and other necessary reagents were purchased from Glen Research Inc. The synthesized phosphoroamidite unit used was dissolved in anhydrous acetonitrile (0.1 M) and applied to a DNA autosynthesizer. The deprotection of the base was conducted by addition of aqueous ammonia (2 mL) and leaving it at room temperature for 12 hours. The subsequent purification was conducted as in Example 14.

MALDI-TOF mass: calcd. 3188.8. found 3188.6.

Melting temperatures (Tm) of double strands of the oligonucleotides obtained above with DNAs having a sequence of 5'-CTCCYCGCCG-3' (SEQ ID NO: 14, Y represents 2'-deoxyadenosine, 2'-deoxyguanosine, 2'-deoxycytidine, or thymidine) complementary to the oligonucleotides were measured. The measurement was conducted in a 10 mM sodium phosphate buffer solution (pH 7.0) containing 0.1 M NaCl and 0.1 mM EDTA using 2 μM of each oligonucleotide.

TABLE 7

| X   | Y | Tm(° C.) | ΔTm(° C.) |
|-----|---|----------|-----------|
| G   | C | 52       | —         |
| G   | A | 37       | −15       |
| G   | G | 36       | −16       |
| G   | T | 39       | −13       |
| cmG | C | 52       | —         |
| cmG | A | 36       | −16       |
| cmG | G | 37       | −15       |
| cmG | T | 36       | −16       |

The Tm (52° C.) of the oligonucleotide containing 2'-deoxy-2-N-carbamoylguanosine (cmG) at the X position with the complementary strand (Y=C) was equivalent to that of the oligonucleotide containing 2'-deoxyguanosine (G) at the X position.

On the other hand, in the most stable mismatching, the Tm (36° C., Y=G, T) of the oligonucleotide containing cmG at X position was lower than that (39° C., Y=T) of the oligonucleotide containing G at the X position by 3° C. It is obvious by this result that an oligonucleotide containing cmG is improved in the mismatching base-discriminating ability.

The invention claimed is:

1. An oligonucleotide derivative represented by the following General Formula (1):

[Formula 1]

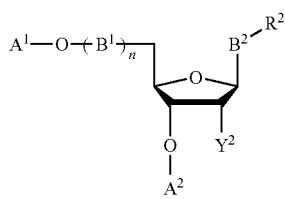

(1)

(where $A^1$ and $A^2$ may be the same or different and each represent a hydrogen atom, a hydroxyl group, an alkyl group, which may be substituted by a substituent; n represents an integer of 10 to 50; $Y^2$ represents a hydrogen atom, a hydroxyl group, an alkoxy group, or a 2-cyanoethoxy group or may be bound to the carbon atom at the 4'-position of the ribose to form a ring; $B^2$ represents a natural or non-natural nucleotide base; $R^2$ represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); and $B^1$ represents a substituent represented by the following General Formula (2):

[Formula 2]

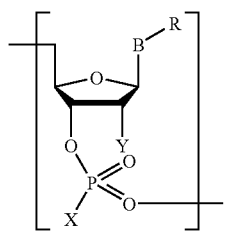

(2)

where B represents a natural or non-natural nucleotide base; R represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); X represents an oxygen ion, a sulfur ion, $BH_3$, $OCH_3$, or $CH_3$; and Y represents a hydrogen atom, a hydroxyl group, an alkoxy group, or a 2-cyanoethoxy group or may be bound to the carbon atom at the 4'-position of the ribose to form a ring, wherein at least one of R and $R^2$ is not a hydrogen atom).

2. The oligonucleotide derivative according to claim 1, wherein the oligonucleotide derivative is used as a probe.

3. A microarray for detection of gene, the microarray comprising a support immobilized with at least an oligonucleotide derivative according to claim 1.

4. A DNA chip, the DNA chip comprising a support immobilized with at least an oligonucleotide derivative according to claim 1.

5. The DNA chip according to claim 4, wherein the support is controlled pore glass.

6. A method of identifying a nucleotide in a target nucleic acid comprising the steps of:
hybridizing an oligonucleotide derivative represented by the following General Formula (1) to a target nucleic acid in a sample; and
detecting the hybridization product:

[Formula 3]

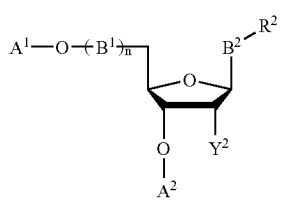

(1)

(where $A^1$ and $A^2$ may be the same or different and each represent a hydrogen atom, a hydroxyl group, an alkyl group, a phosphate group, or a trityl group which may be substituted by a substituent; n represents an integer of 10 to 50; $Y^2$ represents a hydrogen atom, a hydroxyl group, an alkoxy group, or a 2-cyanoethoxy group or may be bound to the carbon atom at the 4'-position of the ribose to form a ring; $B^2$ represents a natural or non-natural nucleotide base; $R^2$ represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); and $B^1$ represents a substituent represented by the following General Formula (2):

[Formula 4]

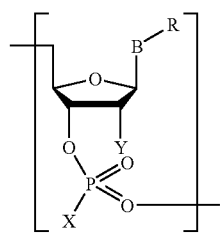

(2)

where B represents a natural or non-natural nucleotide base; R represents a substituent bound to an amino group of the nucleotide base and is a hydrogen atom, an acyl group, a thioacyl group, an alkoxycarbonyl group, an alkoxythiocarbonyl group, a carbamoyl group which may be substituted by an alkyl group, a thiocarbamoyl group which may be substituted by an alkyl group, or an alkyl group (which may be bound to an alkyl group, an alkenyl group, an alkynyl group, or a phenyl group); X represents an oxygen ion, a sulfur ion, $BH_3$, $OCH_3$, or $CH_3$; and Y represents a hydrogen atom, a hydroxyl group, an alkoxy group, or a 2-cyanoethoxy group or may be bound to the carbon atom at the 4'-position of the ribose to form a ring, wherein at least one of R and $R^2$ is not a hydrogen atom).

7. A nucleotide derivative represented by General Formula (17):

[Formula 7]

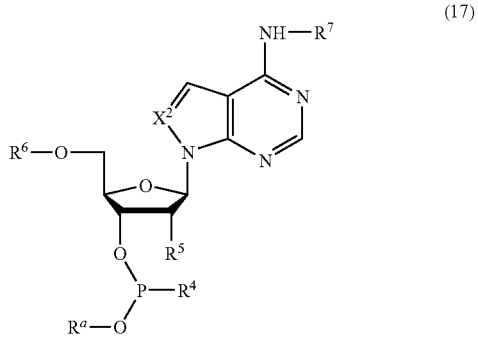

(17)

(where $R^3$ represents a phosphate-protecting group; $R^4$ represents a dialkylamino group having the same or different two alkyl groups each having one to six carbon atoms on its nitrogen atom; $R^5$ represents a hydrogen atom, an alkoxy group, or a trialkylsilyloxy group, a trialkylsilyloxymethoxy group, or a cyanoethyl group which has the same or different alkyl groups each having one to ten carbon atoms or is bound to the carbon atom at the 4'-position of the ribose to form a ring; $R^6$ represents a hydroxyl-protecting group; $R^7$ represents an acyl group (excepting a benzoyl group), a thioacyl group, an alkoxycarbonyl group, an alkoxythiocarbonyl group, a carbamoyl group which may be substituted by an alkyl group, a thiocarbamoyl group; and $X^2$ represents a nitrogen atom or a carbon atom which may have a substituent thereon).

8. A nucleotide derivative represented by Formula (22), (23), or (24)

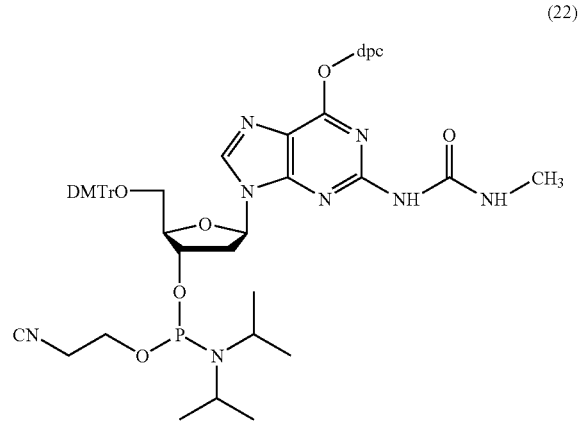

(22)

-continued
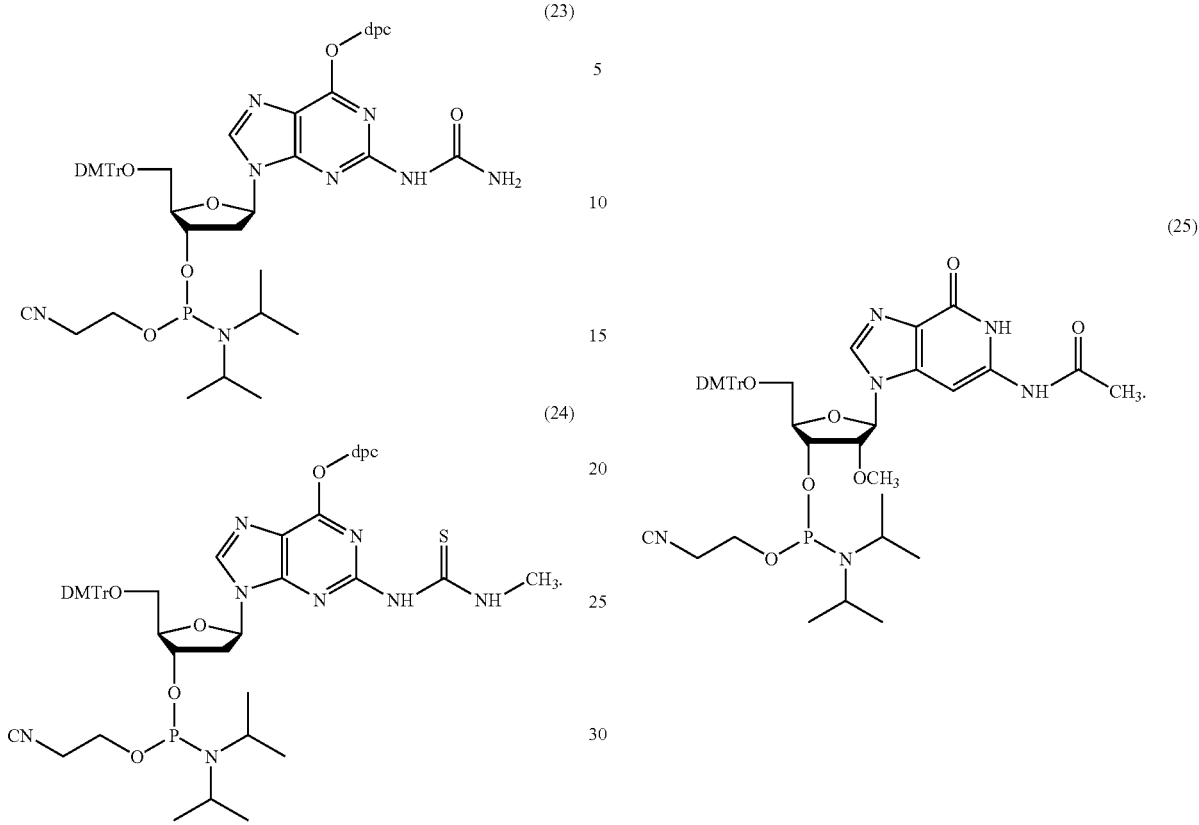
9. A nucleotide derivative represented by Formula (25)

SEQUENCE LISTING

<160> NUMBER OF SEQ ID NOS: 14

<210> SEQ ID NO 1
<211> LENGTH: 13
<212> TYPE: DNA
<213> ORGANISM: Artifical sequence
<220> FEATURE:
<223> OTHER INFORMATION: probe

<400> SEQUENCE: 1
gcctccggtt cat                                                          13

<210> SEQ ID NO 2
<211> LENGTH: 13
<212> TYPE: DNA
<213> ORGANISM: Artifical sequence
<220> FEATURE:
<223> OTHER INFORMATION: probe

<400> SEQUENCE: 2
atgaaccgga ggc                                                          13

<210> SEQ ID NO 3
<211> LENGTH: 13
<212> TYPE: DNA
<213> ORGANISM: Artifical sequence
<220> FEATURE:
<223> OTHER INFORMATION: probe

<400> SEQUENCE: 3
atgaaccaga ggc                                                          13

<210> SEQ ID NO 4
<211> LENGTH: 13
<212> TYPE: DNA
<213> ORGANISM: Artifical sequence
<220> FEATURE:
<223> OTHER INFORMATION: probe

<400> SEQUENCE: 4
atgaactgga ggc                                                          13

<210> SEQ ID NO 5
<211> LENGTH: 15
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (7)..(7)
<223> OTHER INFORMATION: deoxy-6N-acetyl-7-deazaadenosine, or
      2'-deoxy-6N-acetyl-8-aza-7-deazaadenosine

<400> SEQUENCE: 5
tacctanata ccata                                                        15

<210> SEQ ID NO 6
<211> LENGTH: 14
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (8)..(8)

```
<223> OTHER INFORMATION: thymidine, 2'-deoxycytidine,2'-deoxyadenosine,
      2'-deoxyguanosin

<400> SEQUENCE: 6
atggtgtnta ggta                                                      14

<210> SEQ ID NO 7
<211> LENGTH: 15
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (2)..(2)
<223> OTHER INFORMATION: 2'-deoxy-6N-acetyl-8-aza-7-deazaadenosine
<220> FEATURE:
<221> NAME/KEY: misc_feature
<222> LOCATION: (6)..(6)
<223> OTHER INFORMATION: 2'-deoxy-6N-acetyl-8-aza-7-deazaadenosine
<220> FEATURE:
<221> NAME/KEY: misc_feature
<222> LOCATION: (7)..(7)
<223> OTHER INFORMATION: 2'-deoxy-6N-acetyl-8-aza-7-deazaadenosine
<220> FEATURE:
<221> NAME/KEY: misc_feature
<222> LOCATION: (8)..(8)
<223> OTHER INFORMATION: 2'-deoxy-6N-acetyl-8-aza-7-deazaadenosine
<220> FEATURE:
<221> NAME/KEY: misc_feature
<222> LOCATION: (10)..(10)
<223> OTHER INFORMATION: 2'-deoxy-6N-acetyl-8-aza-7-deazaadenosine
<220> FEATURE:
<221> NAME/KEY: misc_feature
<222> LOCATION: (13)..(13)
<223> OTHER INFORMATION: 2'-deoxy-6N-acetyl-8-aza-7-deazaadenosine
<220> FEATURE:
<221> NAME/KEY: misc_feature
<222> LOCATION: (15)..(15)
<223> OTHER INFORMATION: 2'-deoxy-6N-acetyl-8-aza-7-deazaadenosine
<220> FEATURE:
<221> NAME/KEY: misc_feature
<222> LOCATION: (3)..(3)
<223> OTHER INFORMATION: 2'-deoxy-4N-acetylcytidine
<220> FEATURE:
<221> NAME/KEY: misc_feature
<222> LOCATION: (4)..(4)
<223> OTHER INFORMATION: 2'-deoxy-4N-acetylcytidine
<220> FEATURE:
<221> NAME/KEY: misc_feature
<222> LOCATION: (11)..(11)
<223> OTHER INFORMATION: 2'-deoxy-4N-acetylcytidine
<220> FEATURE:
<221> NAME/KEY: misc_feature
<222> LOCATION: (12)..(12)
<223> OTHER INFORMATION: 2'-deoxy-4N-acetylcytidine

<400> SEQUENCE: 7
tnnntnnntn nnntn                                                     15

<210> SEQ ID NO 8
<211> LENGTH: 14
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (8)..(8)
<223> OTHER INFORMATION: thymidine, 2'-deoxycytidine, 2'-deoxyadenosine,
      or 2'-deoxyguanosine

<400> SEQUENCE: 8
atggtgtnta ggta                                                      14
```

```
<210> SEQ ID NO 9
<211> LENGTH: 11
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (5)..(5)
<223> OTHER INFORMATION: 2'-O-methyl-2-N-acetyl-3-deazaguanosine

<400> SEQUENCE: 9
cggcngagga g                                                              11

<210> SEQ ID NO 10
<211> LENGTH: 10
<212> TYPE: RNA
<213> ORGANISM: Artifical sequence
<220> FEATURE:
<223> OTHER INFORMATION: probe
<220> FEATURE:
<221> NAME/KEY: misc_feature
<222> LOCATION: (5)..(5)
<223> OTHER INFORMATION: adenosine, guanosine, cytidine, or uridine

<400> SEQUENCE: 10 cuccncgccg                                                                10

<210> SEQ ID NO 11
<211> LENGTH: 10
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (5)..(5)
<223> OTHER INFORMATION: 2'-deoxyadenosine, 2'-deoxyguanosine,
      2'-deoxycytidine, or thymidine

<400> SEQUENCE: 11 ctccncgccg                                                                10

<210> SEQ ID NO 12
<211> LENGTH: 10
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (5)..(5)
<223> OTHER INFORMATION: 2'-deoxy-2-N-carbamoylguanosine

<400> SEQUENCE: 12 cggcnaggag                                                                10
```

```
<210> SEQ ID NO 13
<211> LENGTH: 10
<212> TYPE: DNA
<213> ORGANISM: Artifical sequence
<220> FEATURE:
<223> OTHER INFORMATION: probe
<220> FEATURE:
<221> NAME/KEY: misc_feature
<222> LOCATION: (5)..(5)
<223> OTHER INFORMATION: 2'-deoxy-2-N-methylcarbamoylguanosine

<400> SEQUENCE: 13 cggcnaggag                                                         10

<210> SEQ ID NO 14
<211> LENGTH: 10
<212> TYPE: DNA
<213> ORGANISM: Proboscidea louisianica
<220> FEATURE:
<221> NAME/KEY: misc_feature
<222> LOCATION: (5)..(5)
<223> OTHER INFORMATION: 2'-deoxyadenosine, 2'-deoxyguanosine,
      2'-deoxycytidine, or thymidine

<400> SEQUENCE: 14 ctccncgccg                                                         10
```